United States Patent [19]

Morrison et al.

[11] Patent Number: 5,071,962

[45] Date of Patent: Dec. 10, 1991

[54] NUCLEOTIDE, DEDUCED AMINO ACID SEQUENCE, ISOLATION AND PURIFICATION OF HEAT-SHOCK CHLAMYDIAL PROTEINS

[75] Inventors: Richard P. Morrison; Harlan D. Caldwell, both of Hamilton, Mont.

[73] Assignee: The United States of America as represented by the Department of Health and Human Services, Washington, D.C.

[21] Appl. No.: 531,317

[22] Filed: May 31, 1990

[51] Int. Cl.$^5$ ............ A61K 35/14; C07K 3/00; C07K 13/00; C07K 15/00
[52] U.S. Cl. ............ 530/387; 530/808; 530/809; 435/240.27
[58] Field of Search ............ 530/387, 825; 435/70.21

[56] References Cited

PUBLICATIONS

Morrison R. P. et al., J. Exp. Med. 169:663–75, Mar. 1989, "Ocular Hypersensitivity...".
Morrison, R. P. et al. J. Exp. Med. 170:1271–83, Oct. 1989, "The 57 KDa Chlamydial...".
Kohler G. and Millstein C., Nature 256:495–7, 1975, "Continuous Cultures of Fused Cells...".

Primary Examiner—Margaret Moskowitz
Assistant Examiner—Thomas Cunningham
Attorney, Agent, or Firm—Cushman, Darby & Cushman

[57] ABSTRACT

The present invention relates to novel polypeptides comprising a unique "chlamydial-specific" primary structural conformation and one or more of the biological properties of eukaryotic or prokaryotic stress-response proteins which are characterized by being the expressed products of an endogenous or exogenous DNA sequence in a eukaryotic or prokaryotic host cell. Sequences coding for part or all of the amino acid residues of the chlamydial HypA or HypB protein or for analogs thereof may be incorporated into autonomously replicating vectors employed to transform or transfect suitable procaryotic or eukaryotic host cells such as bacteria or vertebrate cells in culture. The HypB protein is a member of the family of stress response proteins referred to as HSP60. Products of expression of the DNA sequences display the identical physical, immunological, and histological properties as the chlamydial proteins isolated from natural, non-recombinant, organisms.

4 Claims, 35 Drawing Figures

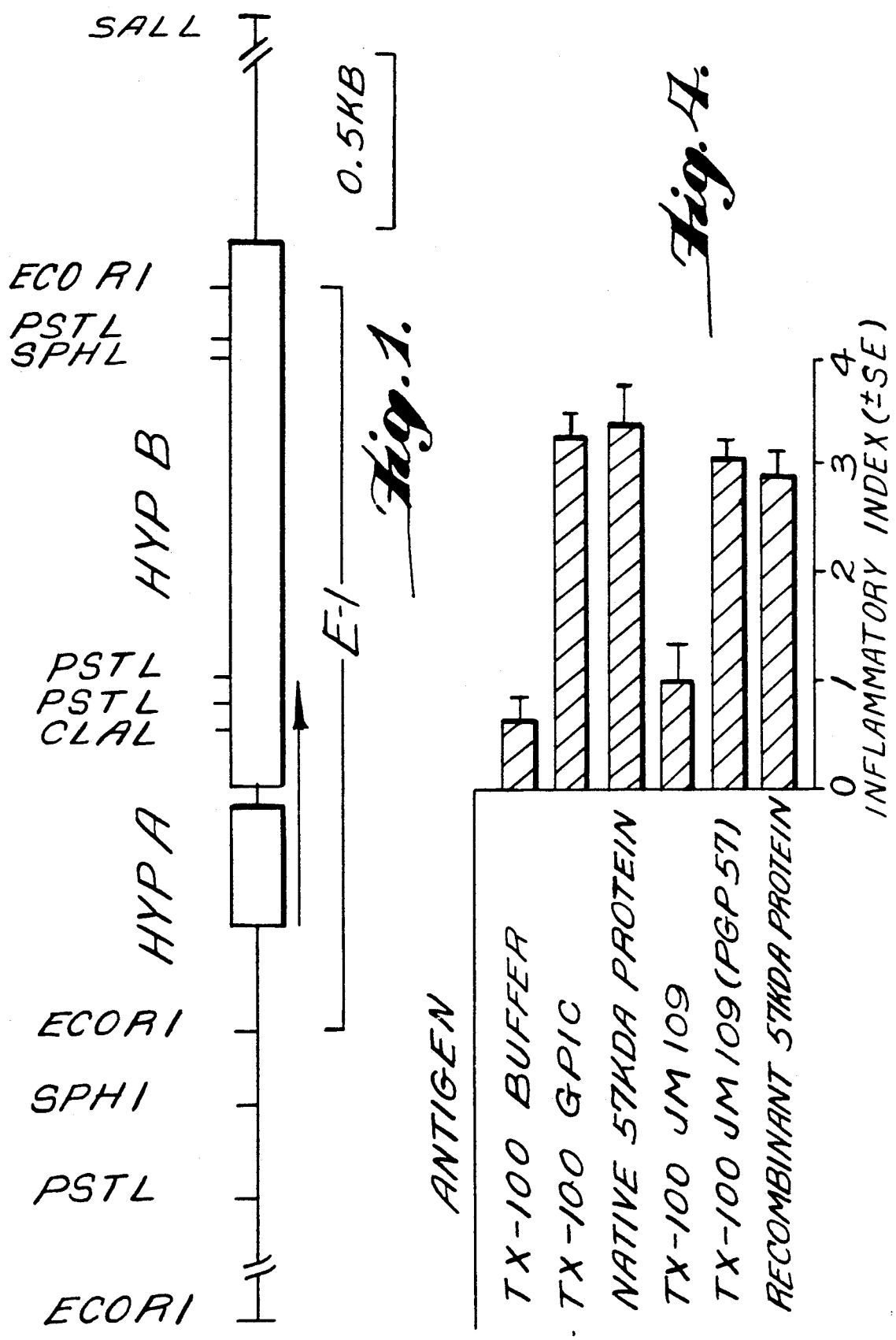

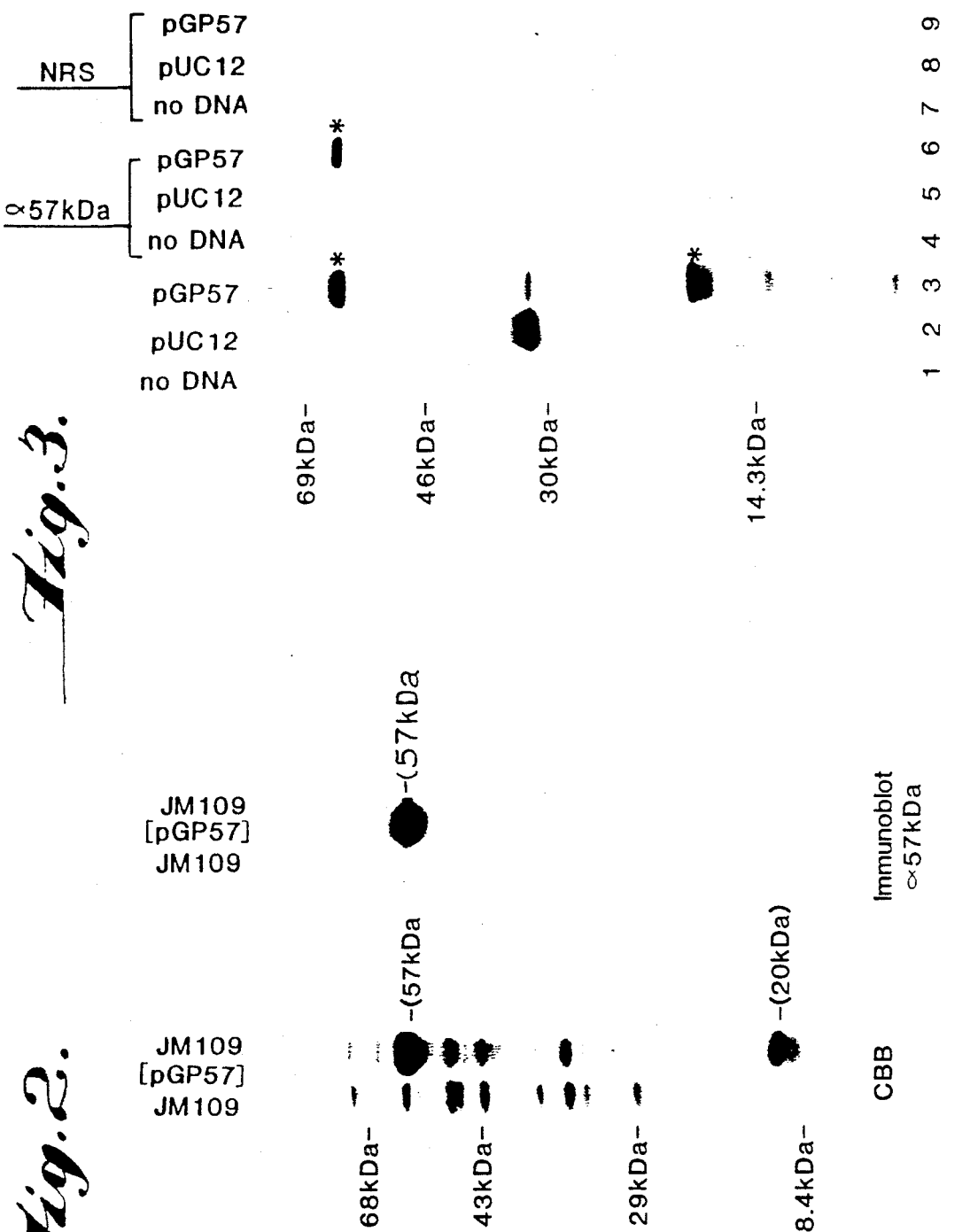

Fig. 5A.

```
GAATTCTTAACAAGAAGATAACGCTCTCGAATCGTACATGAACTTCTTAAAAGTGGTGGCTCCGAC
TATGGCAACCAGGAGCCCATATACAAGGCCTTTCCTTCATAGAGAAAAATTCAAGAGTATCAT
                    -10
GATATTAAGTGCTAAATCATTGCCAAAAACGAGACTTGGTATCGTTCCTGAGAACGGCA
       M   S   D   Q   A   T   T   L   R   I   K   P   L   G   D   R
      AAC ATG TCA GAT CAA GCA ACG ACC CTT AGG ATT AAG CCC CTG GGC GAT AGA
      hypA
       1
   S   T   A   R   G   G   I   I   L   P   D   T   A   K   K   K   Q
  TCT ACA GCG CGC GGC GGC ATC ATT TTA CCT GAT ACA GCA AAG AAA AAA CAG
               30                                                 90
   T   G   K   R   D   K   D   G   N   V   L   P   F   E   V   T   V
  ACT GGA AAA CGA GAT AAA GAT GGC AAC GTC CTA CCT TTT GAA GTT ACC GTG
   A   G   Q   E   L   T   V   T   G   E   E   Y   D   G   E   Q   E
  GCG GGA CAA GAA CTT ACC GTT GAT GGT GAG GAG TAC GTC ATT GTT CAG GAA
                                                             60
                                                              1
                                                              M   A   K
  GAGAAATCATTATTATAGATTGCAAAAAGTAAGGAGCACAAAAAACA ATG GCA AAA
                                                            hypB     30
   K   K   I   H   K   G   V   K   T   L   A   E   A   V   K   V   T
  AAA AAA ATC CAT AAA GGA GTT AAA ACC CTT GCA GAA GCT GTA AAA GTA ACC
   I   D   K   S   F   G   S   P   Q   V   K   D   G   V   T   V
  ATC GAT AAA AGC TTT GGT TCT CCT CAA GTT ACC AAA GAT GGC GTA ACT GTC
   H   E   N   M   G   A   Q   M   V   K   E   V   A   S   K   T   A
  CAT GAG AAC ATG GGA GCT CAA ATG GTA AAA GAA GTC GCT AGC AAA ACT GCA
```

Fig. 5B.

```
TTCCATTAGAAATCTTGAAGAAGTCCGGATTGGA  -211
                -35
CTTTAATTAAACAACTAAGAAAGTAGCACTT  -108

AAGTCTCTTTAGAACAAGAACACAAGGAGCTTAT  -4

I   L   V   K   R   E   E   E   D
ATT TTA GTG AAA AGA GAA GAA GAA GAT  75

D   R   A   E   V   L   V   L   G
GAT CGA GCA GAG GTA TTA GTC CTA GGC  153

G   D   T   V   L   I   D   K   Y
GGT GAT ACT GTT TTA ATA GAT AAA TAC  231

S   E   V   M   A   V   L   K  STOP
AGC GAA GTT ATG GCA GTT CTC AAG TAA  309

N   I   K   Y   N   E   D   A   R
AAT ATT AAA TAT AAC GAA GAC GCC AGA  398

L   G   P   K   G   R   H   V   V
TTA GGT CCT AAA GGC CGT CAT GTG GTT  476

A   K   E   I   E   L   E   D   K
GCT AAA GAA ATT GAG CTC GAA GAC AAG  554
                          90

D   K   A   G   D   G   T   T   T
GAT AAA GCT GGT GAT GGA ACT ACA ACA  632
```

Fig. 5C.

```
  A   T   V   L   A   E   A   I   Y   S   E   G   L   R   N   V   T   A
 GCT ACT GTT CTT GCA GAA GCT ATC TAC AGT GAA GGA TTG AGA AAC GTA ACT GCA
             120

R   G   I   D   K   A   V   K   V   V   D   E   I   K   K   I   S
 AGA GGC ATT GAT AAG GCA GTA AAA GTC GTT GAT GAA ATC AAA AAA ATT AGT

I   A   Q   V   A   T   I   S   A   N   N   D   A   E   I   G   N   L
 ATA GCT CAA GTA GCG ACT ATT TCT GCA AAT AAT GAT GCT GAA ATC GGT AAT CTT
                 150                         180

G   K   N   G   S   I   T   V   E   E   A   K   G   F   E   T   V   L
 GGC AAA AAC GGC TCT ATT ACT GTT GAA GAA GCT AAA GGT TTC GAA ACT GTC CTC
                                                             210

N   R   G   Y   L   S   Y   F   S   T   N   P   E   T   Q   E   C
 AAC CGC GGA TAC CTA TCC AGC TAC TTC TCT ACA AAT CCT GAA ACA CAA GAA TGT

I   Y   D   K   K   I   S   G   I   K   D   F   L   P   V   L   Q   Q
 ATC TAT GAT AAA AAA ATT TCC GGA ATC AAA GAT TTT CTA CCA GTT TTA CAA CAA

L   I   A   E   A   P   G   F   G   E   A   L   A   T   R   K   A   M   L   V   D
 CTT ATC ATT GCT GAA GCT CCT GGA TTT GGT GAA GCT TTA GCT ACT AGA AAA GCT ATG TTA GTA AAC

C   A   V   K   A   E   L   G   M   K   L   E   N   T   T   L   A   M   L   E   D
 TGT GCA GTA AAA GCT GAA CTT GGC ATG AAG CTT GAG AAC ACA ACT CTA GCT ATG TTA GAA GAC
 300

L   I   S   E   E   L   G   M   K   V   E   G   L   I   A   M   L
 CTC ATC AGC GAG GAG CTT GGC ATG AAG GTT GAA GGT CTT ATC GCT ATG TTA
                 330

S   K   E   D   T   T   I   V   E   G   L   G   S   K   E   D   I   E
 TCC AAA GAA GAT ACA ACA ATT GTT GAA GGT CTT GGC AGC AAA GAA GAT ATT GAA
```

```
G   A   N   P   M   D   L   K
GGC GCC AAT CCT ATG GAC CTC AAA   710

K   P   V   Q   H   H   K   E
AAA CCC GTA CAA CAT CAC AAA GAA   788

I   A   E   A   M   E   K   V
ATC GCC GAA GCC ATG GAA AAA GTT   866

D   V   V   E   G   M   N   F
GAC GTT GTC GAA GGT ATG AAT TTC   944

V   L   E   E   A   L   V   L
GTT TTA GAA GAA GCT CTC GTG CTT   1022
240

V   A   E   S   G   R   P   L
GTA GCA GAA TCA GGA CGT CCC CTA   1100
                270

R   L   R   A   G   F   R   V
AGA CTA CGT GCT GGA TTC AGA GTG   1178

I   A   I   L   T   G   G   Q
ATC GCT ATT TTA ACT GGT GGT CAA   1256

G   K   A   K   K   V   I   V
GGA AAA GCT AAA AAA GTC ATC GTT   1334

S   R   C   E   S   I   K   K
TCT CGC TGC GAA AGT ATC AAA AAA   1412
```

Fig. 5D.

```
  Q   I   E   D   S   T   S   D   Y   D   K   E   K   L   Q   E   R   L
 CAA ATC GAA GAC AGT ACT TCT GAT TAC GAC AAA GAA AAA CTC CAA GAA CGT TTA
                             360                     390

V   I   R   V   G   A   A   T   E   I   E   M   K   E   K   D   R
 GTA ATC CGT GTA GGA GCT GCT ACA GAA ATC GAA ATG AAA GAG AAA GAC AGA
                                                                 420

L   A   A   V   E   E   G   I   L   P   G   G   T   A   L   V   R
 CTT GCT GCA GTT GAA GAA GGT ATT CTA CCT GGC GGT ACA GCT TTA GTT CGC

I   P   I   L   T   N   E   D   E   Q   I   G   A   R   I   V   L   K
 ATT CCT ATT CTT ACA AAT GAA GAT GAG CAA ATC GGA GCA CGT ATT GTT CTC AAA

I   A   A   N   A   G   K   E   G   A   I   I   C   Q   Q   V   L   S
 ATT GCA GCC AAT GCT GGT AAA GAA GGC GCT ATC ATC TGT CAA CAA GTG CTT TCT

A   L   R   D   A   Y   T   D   M   I   E   A   G   I   L   D   P   T
 GCT TTA CGC GAT GCT TAC ACC GAC ATG ATT GAG GCA GGA ATT CTC GAT CCA ACT
             510

S   A   A   S   V   A   G   L   L   T   T   E   A   L   I   A   D
 AGC GCA GCT TCT GTA GCT GGG CTT CTA ACA ACA GAA GCT TTA ATT GCC GAT
                                 540

A   P   A   M   P   G   A   G   M   D   Y  STOP
 GCT CCC GCA ATG CCA GGC GCA GGA ATG GAT TAT TAA TCCTTAATTAGAGAGCATTTCT

TGAGAAGAAGGGGCCTTTTTATTTCTAATATTCTTTCTTCATCTATGTTGGAAACCAAGATAAATCA
```

Fig. 5E.

```
A   K   L   S   G   G   V   A
GCT AAA CTT TCC GGA GGC GTA GCT  1490

V   D   D   A   Q   H   A   T
GTA GAT GAT GCT CAG CAT GCA ACT  1568

C   I   P   T   L   E   A   F
TGC ATC CCT ACT TTA GAA GCT TTC  1646
            450

A   L   S   A   P   L   K   Q
GCA TTA TCC GCT CCA TTA AAG CAA  1724
                            480

R   S   S   S   E   G   Y   D
CGC TCC TCT AGC GAA GGC TAT GAT  1802

K   V   T   R   C   A   L   E
AAA GTT ACA CGT TGT GCT TTA GAA  1880
==================

I   P   E   E   K   S   S   S
ATT CCT GAA GAG AAA TCC TCT TCT  1958

CTAATATTATAAGGTTCCTTTCATGCATCT   2049

TATTCTCATCATGCATGTTTAAACTTTTAAA  2152
```

A
```
          1                              30                              60
HypA   MSDQATTLRIKPLGDRILVKREEDSTARGGIILPDTAKKKQDRAEVLVLGTGKRDKDGNVL
        ::  :: ::::: :::::  ::::  : ::::      :: ::  :::: :::::
HtpA   ------MK.R..H..VV.R.L..ER.SA...VI..S.AE.PS.G..ISV.P..PLDN.E.R
        ::  :: ::::: :::::  ::::  : ::::      :: ::  :::: :::::
GroES  ------MN.R..H..VI...K.VETKSA...V.TGS.AA.ST.G...AV.N.RILEN.E.K

B
          1                              30                              60
HypB   MAAKNIKYNEDARKKIHKGVKTLAEAVKVTLGPKGRHVVIDKSFGSPQVTKDGVTVAKEIEL
        ::  :: ::::: ::                                   ::
HtpB   ....VL.FSHEVLHAMSR..EV..N.................A.TI.....S........
        ::  :: :::::  :::::  ::                           ::
GroEL  ....DV.FGN...V.MLR..NV...D............N..L....A.TI.....S..R..
        :::  ::: ::::: ::                       ::          ::
TB 65K ---.T.A.D.E..RGLER.LNA..D...............N..LE.KW.A.TI.N...SI.......
              ::          ::
Hsp60* SSH.EL.FGVEG.ASLL..E......AA.......N.LEQP..P.KI........S.V.
```

Fig. 6B.

```
                                    90
PFEVTVGDTV-LIDKYAGQELTVDGEEYVIVQESEVMAVL-K
  ::           :    :::      ::
SLD.K...QI-.FG....T.VKLA.D..IVMR.DDI.G.IE.
  ::                :     ::   :::
.LD.K....I.IEN.G.GVKSEKI.N..VL.MS..DIL.IVEA 120
                                    90
EDKHENMGAQMVKEVASKTADKAGDGTTTATVLAEAIYSEGLRNVTAGANPMDLKRGI
                                                       ::
...F................R.S.D...............Q..LV..IKA.I..M......
                                                       ::
...F................AN.A................Q...IT...KA.A..M......
  ::                                                   :
..PY.KI..EL......K..D.V..................Q.LVR.....A....LG....
  ::             ::                        ::          ::
K..F....KLLQ.....NEA.............S.....GR..FT.SVK..A..C.....R..S
```

Fig. 6c.

```
        121                            150                             180
HypB    DKAVKVVDEIKKISKPVQHHKEIAQVATISANNDAEIGNLIAEAMEKVGKNGSITVEEAK
HtpB    ....TAA.A.L......CKDQ.A.....G.....S.KS..DI...........E.V....DGS
GroEL   ....TAA.E.L.AL.V.CSDS.A.....G.....S.ETV.K......D.....E.V....DGT
TB 65K  E...EK.TETLL.GA.E.ETKEQ...AT.A...-G.QS...D......D....NE.V.....SN
Hsp60   QV..EK.IEFLSANK.EITTSE..............G.SHV.K.L.S......E.V..IR.GR 241                            270                             300
HypB    AESGRPLLIIAEDIEGEALATLVVNRLRAGFRVCAVKAPGFGDRRKAMLEDIAILTGGQLI
HtpB    .K................V..................NI.GVVK.A...........Q..V.....KV.
GroEL   .KA.K.............V............A....TI.GIVK.A...........Q....T....TV.
TB 65K  IGA.K..............V......S.....KI.GT.KSV...............Q.M........V.
Hsp60   NQ.R...........VD.....ACIL.K..GQVK..............N..NTIG...V.....TVF
```

Fig. 6D.

```
                     210                                                                240
GFETVLDVVEGMNENRGYLSSYFSTNPETQECVLEEALVLIYDKKISGIKDELPVLQQV
.L.NA.E.....Q.D......P..IN.QQNMSAE..NPFI.LV......N.RELI.L.EN.
 ::                  ::            ::         ::   :::  :  ::
.LQDE........Q.D......P..INK...GAVE...SPFI.LA......N.REM....EA.
 ::           ::      ::          ::          ::    ::      ::
T.GLQ.ELT....R.DK..I.G..V.D..R..A...DPYI.LVSS.V.TV..L..L.EK.
  ::         ::   : :    :   :  :    ::    ::     ::   :   ::
TL.DE.E.T....R.D..FI.P...I.D.KSSKVEF.KP.L.LSE....S.Q..I..A.EIS
 :  :  :      : :   :     : :       :   :  ::     :    :   :::

330                                                                360
SEELGMKLENTTLAMLGKAKKVIVSKEDTTIVEGLGSKEDIESRCESIKKQIE-DSTSD
 ::                  ::            ::         ::   :::  :  ::
...V.LS..AAS.DD...S..R.V.T.D......ID.S.DAG...KN.V..Q.R.E...-N.S..
   :    ::  ::    :   : : :       :: :  ::     :   : :      : :
...I..E..KA..ED...Q..R.VIN.DT....ID.V.EEAA..QG.VAQ.RQ....-EA...
    :   ::   ::    :   ::  ::     ::   ::   ::   ::   :      ::
...V.LT...AD.SL....R..V.T.DE........A.DTDA..AG.VAQ.RQE...-N.D...
   :     ::  ::     :  : :  :        : ::   ::   ::    :     :
T...DL.P..QC.IEN..SCDSIT.T....V.LN.S.P..A.QE.I.Q..GS.DITT.NS
     :: :  :  ::      :   :      :  : :   : :   :   :     ::
```

Fig. 6E.

```
        361                                390                          420
HypB    YDKEKLQERLAKLSGGVAVIRVGAATEIEMKEKKDRVDDAQHATLAAVEEGILPGGGTAL
HtpB    ..........................A.......K......V......A..E..L...R......VV....V..
                                    ::                      ::         ::
GroEL   ..R....Q.V..A........K......V......A..E..L...R......VVA...V..
                                                                    ::
TB 65K  ..R..........A........KA.........V.L..R.H..IE..VRNAK......VA...VT.
                                  ::                  ::    ::
Hsp60   ..E.....................................G.S.V.VG....Y...LN..R..............

481                                510                          540
HypB    --GYDALRDAYTDMIEAGILDPTKVTRCALESAASVAGLLLTTEALIADIPE-EKSSSAP
HtpB    --...N.ATGE.G.....M................T..QN....I.....MI...CMVTEA..K-K.EE..M..
                                                      ::        ::    ::::
GroEL   --...N.ATEE.GN..DM................S..QY..........MI...CMVT.L..K-NDAADLG
                ::        ::                                        ::
TB 65K  --...LN.QTGV.E..LLA..VA....V......S..QN....I..F.....VV..K..K..A..VPG
              ::    ::                                                ::
Hsp60   AK.....SKSE....LAT..I..F..V.SG.VD.SG...S..A....VA.V.A..PPAAAG.G
```

Fig. 6F.

```
                               450                               480
VRCIPTLEAFIPILTNEDEQIGARIVLKALSAPLKQTAANAGKEGAIICQQVLSRSSSE-
 ..:.:: ::..:                   ::      ::
I.VLKS.DS-VEV-E...QRV.VE.ARR.MAY...S..VK.T.VQA.VVADK..NHKDVNY
                                  ::   :::  :
I.VASK.ADLRG--Q.Q.QNV.IKVA.R.ME...R...VL.C.E.PSVVANT.KG-GDGNY
                                        ::       ::
LQAA...DEL--K..-EG..AT..N..KV..E......F.S.L.PGVVAEK.RNLPAGH-
 ::  ::           ::                  ::          ::      ::
.KASRV.DE-V-VVD.F.QKL.VD.IR..ITR.A...IE...E..SV.IGKLIDEYGDDF

AMPGAGMDY

GGGDM.GMGGMGGMGGMM

.AG.M.GMGGMGGMM

GGDMG...F

G...GMPGMPGMM
```

Fig. 7A.

```
                                                                                                              -88 ..GAAC
             hypA
              1
              M   S   D   Q   A   T   T
-39 CGAGGCCTCGTAGAATATAAAAATACGAGGAGCTTAAAC ATG TCA GAT CAA GCA ACG ACC
                     20
     V   K   R   E   E   E   A   S   T   A   R   G   G   I   I   L   P
 55 GTT AAA AGA GAA GAA GAA GCT TCC ACT GCA AGA GGC GGA ATC ATT CTT CCT
                                                                 60
     V   L   A   L   G   T   G   K   K   D   D   K   G   Q   Q   L   P
139 GTT TTA GCT CTA GGA ACA GGC AAA AAA GAT GAT AAA GGG CAG CAA CTT CCT
                         80
     D   K   Y   S   G   Q   E   L   T   V   E   G   E   E   Y   V   I
223 GAT AAA TAT TCT GGC CAA GAA CTT ACT GTC GAA GGT GAA GAG TAC GTC ATC
                                                 1
     STOP                                        hypB M   V   A   K   N   I
307 TAA AAACTAAGAGAGTGAAGAAGATTAAGGAGCGCATCA ATG GTC GCT AAA AAC ATT
                     20
     K   G   V   K   T   L   A   E   A   V   K   V   T   L   G   P   K
398 AAA GGA GTT AAG ACT TTA GCT GAA GCT GTA AAA GTC ACT CTA GGG CCT AAA
                                                                 60
     S   P   Q   V   K   D   G   V   T   V   A   K   E   E   V   E   L
482 TCC CCT CAA GTA AAG GAT GGT GTT ACC GTT GCG AAA GAA GTT GAG CTT
                         80
     V   K   E   V   A   S   K   T   A   D   K   A   G   D   G   T   T
566 GTC AAA GAA GTC GCC AGC AAA ACT GCT GAC AAA GCT GGA GAC GGA ACT ACA
```

Fig. 7B.

ACGTTCTATGGTGGAAATCTTTGGTAGCGGAGCAAAGCCGGACCA

```
    L   K   I   K   P   L   G   D   R   I   L
    CTC AAG ATT AAA CCT TTG GGA GAT AGA ATT TTA
                    40

D   T   A   K   K   K   Q   D   R   A   E
    GAC ACT GCC AAG AAA AAG CAA GAT AGA GCT GAA

F   E   V   Q   V   G   D   I   V   L   I
    TTT GAA GTT CAG GTT GGT GAC ATC GTT TTA ATT
                                    100

V   Q   M   S   E   V   I   A   V   L   Q
    GTT CAA ATG AGC GAA GTT ATC GCA GTT CTG CAA

K   Y   N   E   E   A   R   K   K   I   Q
    AAA TAC AAC GAA GAA GCC AGA AAG AAA ATT CAA
                        40

G   R   H   V   V   I   D   K   S   F   G
    GGA CGA CAT GTT GTC ATA GAT AAA AGC TTC GGA

A   D   K   H   E   N   M   G   A   Q   M
    GCC GAC AAA CAT GAA AAT ATG GGC GCT CAA ATG
                                    100

T   A   T   V   L   A   E   A   I   Y   T
    ACA GCT ACT GTT CTT GCT GAA GCT ATC TAT ACA
```

Fig. 7c.

```
      E   G   L   R   N   V   T   A   G   A   N   P   M   D   L   K   R
 650 GAA GGA TTA CGC AAT GTA ACA GCT GGA GCA AAT CCA ATG GAC CTC AAA CGA
                                         140
      Q   I   K   K   I   S   K   P   V   Q   H   H   K   E   I   A   Q
 734 CAA ATC AAA AAA ATC AGC AAG CCT GTT CAG CAT CAT AAA GAA ATT GCT CAA
                     160
      I   G   N   L   I   A   E   A   M   E   K   V   G   K   N   G   S
 818 ATC GGG AAT CTG ATT GCT GAA GCA ATG GAG AAA GTT GGT AAA AAC GGC TCT
                                                             200
      V   L   D   V   V   E   G   M   N   F   N   R   G   Y   L   S   S
 902 GTT TTG GAT GTT GTT GAA GGA ATG AAT TTC AAT AGA GGT TAC CTC TCT AGC
                             220
      V   L   E   D   A   L   V   L   I   I   Y   D   K   K   I   S   G   I
 986 GTA TTA GAA GAC GCT TTG GTT CTA ATC ATT TAC GAT AAG AAA ATT TCT GGG ATC
      E   S   G   R   P   L   I   I   A   E   D   I   E   G   E   A
1070 GAA TCC GGC CGT CCT CTT ATT ATA GCA GAA GAC ATT GAA GGC GAA GCT
                                         280
      G   F   R   V   C   A   V   K   A   P   G   F   G   D   R   R   K
1154 GGA TTC CGG GTT TGC GCA GTT AAA GCT CCA GGC TTT GGA GAT AGA AGA AAA
      G   Q   L   I   S   E   E   L   G   M   K   L   E   N   A   N   L
1238 GGT CAA CTC ATT AGC GAA GAG TTG GGC ATG AAA TTA GAA AAC GCT AAC TTA
                                                             340
      S   K   E   D   T   T   I   V   E   G   M   G   E   K   E   A   L
1322 TCT AAA GAA GAC ACG ACC ATC GTC GAA GGA ATG GGT GAA AAA GAA GCT TTA
                         360
```

Fig. 7D.

```
 G   I   D   K   A   V   K   V   V   V   D
GGT ATT GAT AAA GCT GTT AAG GTT GTT GTT GAT

V   A   T   I   S   A   N   N   D   A   E
GTT GCA ACA ATT TCT GCT AAT AAT GAT GCA GAA
                    180
 I   T   V   E   E   A   K   G   F   E   T
ATC ACT GTT GAA GAA GCA AAA GGA TTT GAA ACC

Y   F   A   T   N   P   E   T   Q   E   C
TAC TTC GCA ACA AAT CCA GAA ACT CAA GAA TGT
                                    240
 K   D   F   L   P   I   L   Q   Q   V   A
AAA GAT TTC CTT CCT ATT TTA CAA CAA GTT GCT
260
 L   A   T   L   V   V   N   R   I   R   G
TTA GCT ACT TTG GTC GTG AAC AGA ATT CGT GGA

A   M   L   E   D   I   A   I   L   T   G
GCT ATG TTG GAA GAC ATC GCT ATC TTA ACT GGC
                    320
 A   M   L   G   K   A   K   K   V   I   V
GCT ATG TTA GGT AAA GCT AAA AAA GTT ATC GTT

E   A   R   C   E   S   I   K   K   Q   I
GAA GCT CGT TGC GAA AGC ATC AAA AAA CAA ATT
                                    380
```

Fig. 7e.

```
       E   D   S   S   D   Y   D   K   E   L   Q   E   R   L   A
1406  GAA GAC AGC TCT GAT TAC GAT AAA GAA CTC CAA GAG CGT CTT GCT

G   A   A   T   E   I   E   M   K   E   K   D   R   V   D   D
1490  GGA GCT GCA ACA GAG ATT GAG ATG AAA GAG AAA GAT CGT GTA GAC GAT
                                          420

G   I   L   P   G   G   T   A   L   I   R   C   I   P   T   L
1574  GGA ATT CTT CCT GGT GGA ACA GCA TTA ATC CGT TGT ATC CCT ACT CTT

E   Q   I   G   A   R   I   V   L   K   A   L   S   A   P   L   K
1658  GAG CAA ATT GGA GCT CGC ATT GTT TTG AAA GCT CTT TCC GCT CCT TTG AAA
                                                                480

I   I   F   Q   Q   V   M   S   R   S   A   N   E   G   Y   D   A
1742  ATC ATC TTC CAA CAA GTT ATG TCC CGT TCT GCG AAC GAA GGA TAT GAT GCA
                                  500

G   I   L   D   P   A   K   V   T   R   S   A   L   E   S   A   A
1826  GGT ATT TTA GAT CCT GCT AAA GTA ACC CGT TCT GCT TTA GAA AGC GCG GCT

L   I   A   E   I   P   E   E   K   P   A   A   P   A   M   P
1910  CTC ATT GCA GAG ATT CCA GAA GAA AAA CCT GCT GCA CCT GCA ATG CCT

1997  CAAATAGATTCTTCGAGCCTTCGTTTCCAAAAGGAACGAGGCTTTTTTAGATTCCTAATATTCTC

2108  TATGTTTAAACTAATCAAGAGCCGCATTCTTCTCATAGCCTGTGTATTGTAGGGTACTTCTGGATAAAA
```

Fig. 7F.

```
K   L   S   G   G   V   A   V   I   R   V
AAG CTC TCT GGT GGA GTA GCA GTC ATT CGC GTT
        400

A   Q   H   A   T   I   A   A   V   E   E
GCT CAA CAT GCT ACA ATC GCT GCT GTT GAA GAA

E   A   F   L   P   M   L   T   N   E   D
GAA GCC TTC TTG CCA ATG TTG ACT AAT GAA GAT
                    460

Q   I   A   A   N   A   G   K   E   G   A
CAA ATT GCT GCA AAC GCA GGA AAA GAA GGT GCT

L   R   D   A   Y   T   D   M   L   E   A
TTG CGT GAT GCA TAC ACA GAT ATG CTT GAA GCT
                                520

S   V   A   G   L   L   L   T   E   A
TCC GTA GCT GGA TTA CTT TTG ACA GAA GCT
        540

G   A   G   M   D   Y   STOP
                    544
GGC GCA GGA ATG GAC TAT TAA TTCCTCTAATGGGAA

TATTCCTCTATCGTAAACATCTAGTGCTTACGACCATCCTTTTC

AAAGAAAGTATTGTT
```

Fig. 9.

```
                 1                                            30
HypA (A)     MSDQATTLKIKPLGDRILVKREEEASTARGGIILPDTAKKKQDRAEVLAL
HypA (GPIC)  .............R...................D...............V.

60                                           90
             GTGKKDDKGQQLPFEVQVGDIVLIDKYSGQELTVEGEEYVIVQMSEVIAVLQ
             ....R.KD.NV......T....T......A......D....E...M...K
```

Fig. 10A.

```
           1                          30                                    60
HypB (A)   MVAKNIKYNEEARKKIQKGVKTLAEAVKVTLGPKGRHVVIDKSFGSPQVTKDGVTVAKEV
HypB (GPIC) .....A.........D......H.....................................I 121                        150                                   180
HypB (A)   DKAVKVVVDQIKKISKPVQHHKEIAQVATISANNDAEIGNLIAEAMEKVGKNGSITVEEA
HypB (GPIC) .............E..............................................

241                        270                                   300
HypB (A)   AESGRPLLIIAEDIEGEALATLVVNRIRGGFRVCAVKAPGFGDRRKAMLEDIAILTGGQL
HypB (GPIC) ...............................................L.A.........

361                        390                                   420
HypB (A)   DKEKLQERLAKLSGGVAVIRVGAATEIEMKEKKDRVDDAQHATIAAVEEGILPGGGTALI
HypB (GPIC) ..................................L........................V 481                        510                                   540
HypB (A)   DALRDAYTDMLEAGILDPAKVTRSALESAASVAGLLLTTEALIAEIPEEKPAAAPAMPGA
HypB (GPIC) ......I......T....C..........................D.....SSS......
```

Fig. 10B.

```
                  90                                        120
ELADKHNMGAQMVKEVASKTADKAGDGTTTATVLAEAIYTEGLRNVTAGANPMDLKRGI
..E........................S.............................

210                                       240
KGFEEVLDVVEGMNENRGYLSSYFATNPETQECVLEDALVLIYDKKISGIKDELPILQQV
.............S...................E........................V 330                                       360
ISEELGMKLENANLAMLGKAKKVIVSKEDTTIVEGMGEKEALEARCESIKKQIEDSSSDY
........TT..................L.S..DI.S........T............

450                                       480
RCIPTLEAFLPMLTNEDEQIGARIVLKALSAPLKQIAANAGKEGAIIFQQVMSRSANEGY
...I.I..................................C...L...SS........

GMDY
....
```

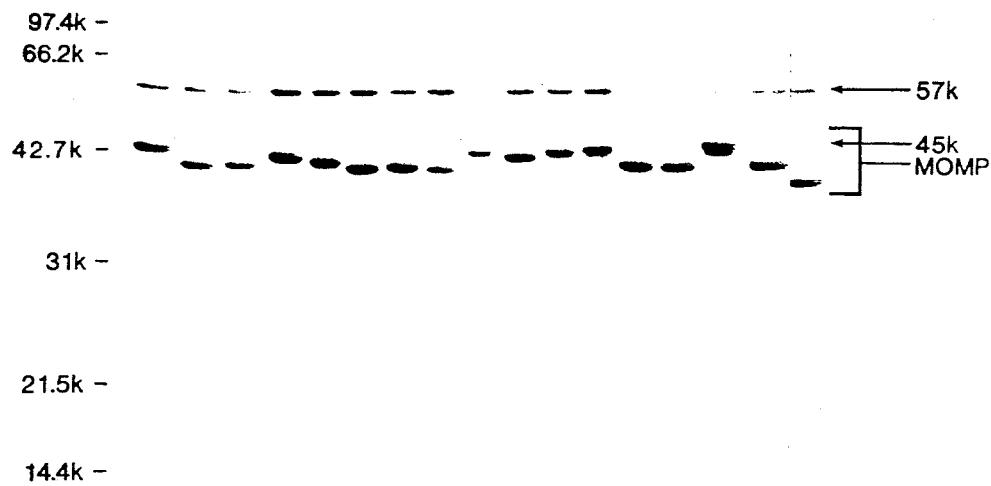

Fig. 14.

NUCLEOTIDE, DEDUCED AMINO ACID SEQUENCE, ISOLATION AND PURIFICATION OF HEAT-SHOCK CHLAMYDIAL PROTEINS

BACKGROUND OF THE INVENTION

1. Field of the Invention

The present invention pertains in general stress-response proteins and to polynucleotides encoding such factors. The present application pertains in particular to the HypB protein of chlamydia bacteria, specifically to the HypB protein from *Chlamydia psittaci* and *Chlamydia trachomatis*, to fragments and polypeptide analogs thereof, and to polynucleotides encoding the same. The HypB protein is a member of a highly conserved family of stress response proteins referred to as HSP60. The HypB protein has a number of acronyms such as the chlamydial GroEL, the chlamydial 57kD antigen and the chlamydial HSP60.

2. Background Information

Members of the genus Chlamydia are obligate intracellular bacteria that are differentiated from all other prokaryotes by their unique intracellular growth cycle. Two species of Chlamydia exist; *C. trachomatis*, strictly a human pathogen, and *C. psittaci*, a pathogen of lower mammals. Chlamydiae primarily infect mucosal epithelia, and in humans *C. trachomatis* causes a formidable group of infections, some of which can progress to severe complications including blindness, infertility, and perhaps arthritis. The most significant of these in the numbers of people afflicted is trachoma, the leading cause of preventable blindness in the world (Jones, Trans. Ophthalmol. Soc.(U.K.), 95, 16(1975)).

Though the pathogenic events that lead to development of severe and often debilitating, post-infection sequelae are not known, an immunological mechanism has been suggested based on studies of human trachoma and sub-human primate models of ocular chlamydial infection (Dawson, *Human Chlamydial Infections* (1978); Grayston, et al., Rev. Infect. Dis., 7,717 (1985); Silverstein, Invest. Ophthalmol., 13, 560 (1974); Collier, Arch. ges. Virusforsch., 22, 280 (1967)).

Early studies in humans and in sub-human primates indicate that prior vaccination with killed chlamydiae frequently results in more severe trachoma upon reinfection (Wang, et al., Am. J. Ophthalmol., 63, 1615 (1967); See Wang, et al., Am. J. Ophthalmol., 63, 1133 (1967); Grayston, et al., Ann. N.Y. Acad. Sci., 98, 352 (1962); Woolridge, et al., Am. J. Ophthalmol., 63, 1645 (1967); Bell, et al., Am. J. Trop. Med. Hyg. 18, 568 (1969)). Moreover, in some individuals with trachoma, chlamydial antigens and DNA are detected in conjunctival tissue in the absence of cultivatable chlamydia (Wilson, et al., Arch. Ophthalmol., 104, 688 (1986); Schachter, et al., J. Infect. Dis., 158 1347 (1989)). These data support the hypothesis of an immunologically mediated pathogenesis.

*C. trachomatis* infection of non-human primates and *C. psittaci* infection of guinea pigs are good model systems for studying chlamydial pathogenesis. Previous studies using these models show that repeated exposure to infectious chlamydiae is necessary to establish the chronic inflammation characteristic of trachoma (Monnickendam, et al., Br. J. Ophthalmol., 64, 284 (1980); Taylor, et al., Invest. Ophthalmol. Vis. Sci., 23, 507 (1982)). Repeated challenge with infectious chlamydiae results in an atypical infection of shortened duration in which chlamydia are difficult to reisolate, and severe ocular disease results; thus suggesting that immune responses are partly protective, but also deleterious. Repeated infection produces a submucosal cellular infiltrate of lymphocytes and macrophages (Patton, et al., J. Infect. Dis., 153, 870 (1986), Monnickendam, supra, and Taylor, supra) like that observed in individuals with trachoma (Hogan & Zimmerman, *Ophthalmic Pathology*, 240–244 (1962)). Collectively, the human and animal studies argue for a pathogenic role of delayed hypersensitivity (DH)[1] in chlamydial disease.

The most direct evidence for DH in pathogenesis of chlamydial disease comes from the observations that a crude extract of viable chlamydiae elicits severe ocular inflammation in immune animals (Watkins, et al., Proc. Natl. Acad. Sci. (USA), 83, 7480 (1986); Taylor, et al., J. Immunol., 138, 3023 (1987)).

In immune guinea pigs, this extract produces an ocular inflammatory response whose histopathology is consistent with human trachoma and chlamydial-induced tubal infertility. Those results support the hypothesis that the host's immune response to chlamydial infection is, in part, deleterious (Moller, et al., Br. J. Vener. Dis. 55, 422 (1979); Hogan, supra, and Watkins, supra).

The inflammation elicited by a chlamydial antigen was clinically and histologically identical to that caused by primary infection which suggested the pathogenesis of the ocular disease was immunologically mediated. This also suggested that the pathogenesis of recurrent chlamydial disease was not due to active infection (Watkins, supra). Identifying hypersensitivity as a major pathogenetic mechanism was important not only in understanding chlamydial associated disease processes but also in establishing future strategies to control chlamydial diseases by immunoprophylaxis. Ocular delayed hypersensitivity has been shown to be induced at mucosal surfaces other than conjunctival-i.e., intestinal or vaginal. Primary chlamydial infection at one mucosal site can elicit a delayed hypersensitivity reaction at either the same or different mucosal surfaces and can contribute to the pathogenesis of chlamydial disease in humans (Watkins, supra).

Recent data suggested that the pathogenesis of guinea pig inclusion conjunctions (GPIC) was mediated by delayed hypersensitivity to an antigen common to strains of both chlamydial species (Watkins, supra).

Prior to the present invention, the biologically active antigen had not been identified. As indicated above, a crude chlamydial extract elicited ocular and dermal delayed hypersensitivity. Lipopolysaccharide (LPS) is a major component of this crude extract and was a suspected antigen. Purified LPS did not elicit hypersensitivity in immune animals but this discovery did not preclude the possibility that the allergen was composed of a complex of LPS with protein, carbohydrate, or lipid (Watkins, supra). Development of a vaccine for trachoma and other chlamydial diseases, which would preclude the deleterious immune response, required identification of the antigen.

The major outer membrane protein (MOMP) is the major structural protein of chlamydiae and is immunogenic (Taylor, et al. J. Immunol., 138, 3023 (1987), supra). Purified MOMP, however, did not elicit an ocular DH response in immune animals. The crude extract of chlamydial elementary bodies (EBs), as indicated above, was biologically active but the exact nature of the extract remained to be determined since neither LPS nor MOMP (components of this extract) elicited an inflammatory response in purified form. Prior to the present invention, the antigenic determinant and inflammatory response elicited by the crude extract was thought to be caused by LPS in conjunction with an alternation in membrane permeability induced by the extraction solution (Taylor, supra). The stimulus for the inflammation response in trachoma has been the subject of ongoing speculation.

The Applicants have isolated and purified a chlamydial antigenic protein responsible for the ocular delayed hypersensitivity inflammatory response from *Chlamydia psittaci* and *Chlamydia trachomatis*. The immunologically bioactive component is the HypB protein of the present invention (Morrison, et al., J. Exp. Med., 169, 663 (1989)). Also described is a HypA antigenic protein (Morrison, et al., supra). The chlamydial gene of the *C. psittaci* and *C. trachomatis* that encodes the HypB protein have been cloned, and the recombinantly produced protein of *C. psittaci* has been shown to elicit an ocular DH response in immune guinea pigs. The sequencing of the gene revealed a close relatedness to the heat-shock or stress proteins GroEL of *Escherichia coli*, HtpB of *Coxiella burnetii*, 65 k of *Mycobacterium tuberculosis*, and Hsp60 of *Saccharomyces cerevisiae*.

While several antigenic detection diagnostic tests for chlamydia are available, none use immunological reagents specific for the HypB protein of the present invention (Chernesky, et al., J. Infect. Dis. 154, 141 (1986); Howard, et al., J. Clin. Microbiol., 23, 329 (1986); Tam, et al., N. Engl. J. Med., 310, 1146 (1984)). The present invention allows for the preparation of peptides analogous to chlamydial-specific determinants for use in monoclonal antibody and monospecific-polyclonal antisera preparation which can be used to identify chlamydiae in clinical specimens or cell culture of chlamydial isolates. Synthetic peptides analogous to the chlamydial-specific determinants can be used in serological assays to diagnose chlamydial infections. The HypB chlamydial protein elicits a cell-mediated immune response in addition to an antibody response. Therefore, the present invention allows for the use of a chlamydial-specific region of the protein as a skin test antigen to diagnose or monitor chlamdial infection; analogous to the use of the TB skin test antigen PPD.

SUMMARY OF THE INVENTION

It is an object of the present invention to provide a segment of a DNA molecule which codes for a HypB and/or a HypA protein derived from the bacteria Chlamydia and the encoded proteins.

It is another object of the present invention to provide a recombinant DNA molecule comprising a vector and a segment of a DNA molecule which codes for a HypB protein derived from the bacteria Chlamydia.

It is a further object of the present invention to provide a host cell stably transformed or transfected with the DNA vector provided by this invention in a manner allowing expression of the protein encoded by the vector.

It is yet another object of the present invention to provide a method of producing the HypB chlamydial antigen on a commercial scale.

It is another object of the present invention to provide a method for the detection of chlamydial HypB protein in clinical specimens, cell cultures or mammals and a method for the diagnosis of chlamydial infection in individuals.

Various other objects and advantages of the present invention will become obvious from the drawings and the detailed description of the invention.

In one embodiment, the present invention relates to a DNA segment encoding all, or a unique portion, of a HypB Chlamydia protein.

In another embodiment, the present invention relates to a DNA segment encoding all, or a unique portion, of a HypA Chlamydia protein.

In another embodiment, the present invention relates to a substantially pure form of a chlamydial HypB protein eliciting a delayed ocular and dermal inflammatory response in mammals.

In a further embodiment, the present invention relates to a recombinantly produced protein having all, or a unique portion, of the amino acid sequence given in FIG. 5 or FIG. 7.

In yet another embodiment, the present invention relates to antibodies specific for the chlamydial HypB protein.

In a further embodiment, the present invention relates to a recombinant DNA molecule comprising a DNA segment encoding all, or a unique portion, of a HypB Chlamydia protein and a vector.

In yet a further embodiment, the present invention relates to a host cell stably transformed with the above recombinant DNA molecule in a manner allowing expression of the protein encoded in the recombinant DNA molecule.

In another embodiment, the present invention relates to a method of producing a Chlamydia HypB protein comprising culturing host cells stably transformed with a recombinant DNA molecule comprising a DNA segment encoding all, or a unique portion, of the HypB Chlamydia protein and vector, in a manner allowing expression of the DNA segment and thereby production of the protein.

In a further embodiment, the present invention relates to a method for the detection of the chlamydial HypB protein in a sample which method comprises contacting a reagent which specifically reacts with the chlamydial HypB protein with the sample under conditions such that reaction between the chlamydial protein and the agent can occur, and detecting the presence or absence of a reaction.

In yet a further embodiment, the present invention relates to a vaccine for mammals against chlamydial disease comprising all, or a unique portion of a Chlamydia HypB protein in an amount sufficient to induce immunization against the disease, and a pharmaceutically acceptable carrier.

The entire contents of all publications mentioned herein are hereby incorporated by reference.

BRIEF DESCRIPTION OF THE DRAWINGS

FIG. 1. Restriction endonuclease map of the 7.2-kb chlamydial DNA insert of pGP57. The internal 2.0-kb EcoRI fragment (E1) is indicated. Open boxes represent the hypA and hypB ORFs. The direction of transcription is indicated by an arrow.

FIG. 2. SDS-PAGE and immunoblot analysis of *E. coli* strain JM109[pUC12] and recombinant strain JM109[pGP57]. (A) Coomassie brilliant blue-stained gel of whole-cell lysates. (B) Immunoblot probed with monospecific polyclonal anti-57-kD serum. Recombinant polypeptides are indicated by approximate $M_r$ values (57k and 20k). Immunological reagents specific for the 20-kD polypeptide were not available, and it was not reactive with hyperimmune anti-GPIC serum.

FIG. 3. In vitro transcription-translation analysis of purified plasmid DNAs and immunoprecipitation of in vitro translated polypeptide. One microgram of purified plasmid DNA was used as suggested by the manufacturer of the commercial in vitro translation kit (Amerisham Corp.). Reaction proceeded at 37° C. for 45 min, followed by a 5 min chase with nonradiolabelled methionine. Reactions mixtures were subjected to SDS-PAGE and analyzed directly by fluorography (lanes 1, 2, and 3), or immunoprecitated with polyclonal monospecific anti-57kD serum (lanes 4, 5, and 6) or normal rabbit serum (lanes 7, 8, and 9), then analyzed. Lanes 1, 4 and 7, no DNA added to reaction mixture: lanes 2, 5 and 8, pUC12 DNA; and lanes 3, 6 and 9, pGP57 DNA. *indicates 57-kD (HypB) and 20-kD (HypA) recombinant polypeptides.

FIG. 4. Ocular DH response elicited by chlamydial antigen preparations. Ocular hypersensitivity was assessed at 24 h after antigen challenge and scored as described in Example 2. TX-100 buffer, TX-100 GPIC and native HypB protein were prepared as described in Morrison et al. The native and recombinant HypB proteins were mixed 1:1 with 2X TX-100 buffer and tested for hypersensitivity. Inflammatory index is the mean response from eight guinea pigs per group. Naive animals were challenged with antigen preparation, and in all instances, the inflammatory index was $\leq 1$.

FIG. 5 (A-F). Nucleotide sequence of the C. psittaci strain GPIC hyp operon. The deduced amino acid sequences of the hypA and hypB ORFs are indicated above the nucleotide sequence. The inferred promoter region ($-35$ region and $-10$ region), ribosomal binding sites (single underscore), and the dyad symmetry (arrows) of the proposed transcription terminator are indicated. The sequence corresponding to the oligonucleotides used for Northern blot analysis are indicated ($====$). Numbers to the right of the figure refer to nucleotide position, and amino acid numbering is above the deduced amino acid sequence.

FIG. 6 (A-F). Comparison of the deduced amino acid sequences of FIG. 6A, (A) the C. psittaci HypA protein and the C. burnetii HtpA and E. coli GroES proteins, and FIG. 6B-F (B) the C. psittaci HypB protein and the C. burnetti HtpB, E. coli GroEL, M. tuberculosis 65 k and S. cerevisiae Hsp60 proteins. Identity is represented by a period (.), conserved amino acid changes by a colon (:) above the amino acid, and gaps introduced for alignment purposes are represented by a hyphen (—). *, the Hsp60 sequence is aligned beginning at amino acid number 22. Amino acid position number does not directly correspond with the amino acid numbers in FIG. 5 because of the inserted gaps needed for alignment.

FIG. 7 (A-F). Nucleotide and deduced amino acid sequence of the C. trachomatis serovar A hyp operon.

FIG. 8. Immunoblot analysis of whole-cell lysates probed with monospecific anti-57-kD serum. Each sample consisted of 20 ug of total protein. Lane 1, C. psittaci strain GPIC; lane 2, C. trachomatis serovar B; lane 3, C. trachomatis serovar L2; lane 4, E. coli strain JM109; lane 5, E. coli strain JM109[pGp57]; lane 6, S. typhimurium strain SL3261; lane 7, N. gonorrhoeae strain MS11;lane 8, R. rickettsii R strain; lane 9, C. burnetii strain Nine Mile; lane 10, B. burgdorferi strain B31; and lane 11, M. tuberculosis strain H37RA.

FIG. 9. Comparison of the the deduced amino acid sequence of the C. trachomatis serovar A HypA protein and the C. psittaci strain GPIC HypA protein. Amino acid identity is indicated by a period (.) and conserved changes by a colon (:).

FIG. 10 (A-B). Comparison of the deduced amino acid sequence of the C. trachomatis serovar A HypB protein and the C. psittaci strain GPIC HypB protein. Amino acid identity is indicated as in FIG. 10.

FIG. 11. Chlamydial specificity of the polyclonal rabbit anti-57-kD antiserum and the anti-45-kD mAb. (A) Coomassie brilliant blue-stained gel of all 15 serovars of C. trachomatis and two strains of C. psittaci, Mn, and GPIC. The MOMPs of each vary in M and are the major staining polypeptides indicated by the bracket. (B) Immunoblot probed with polyclonal monospecific anti-57-kD antiserum. (C) Immunoblot probed with mAb GPIC IV-B1. The polyclonal anti-57-kD and mAb anti-45-kD antibodies were monospecific and reacted with proteins found on all 15 C. trachomatis serovars and two C. psittaci strains. In some serovars the 45-kD protein comigrated with the MOMP (serovars A, C, H, I, and J) and was thus difficult to distinguish on the Coomassie-stained gel. However, it could be distinguished when probed with the anti-45-kD antibody. The 57-and 45-kD proteins are major genus-specific proteins found on EBs.

FIG 12. Immunoblot analysis of immunoaffinity purification of the HypB and 45-kD genus-specific chlamydial proteins. 10 ml of the soluble TX-100 extract of GPIC EBs ($10^{10}$ EBs) were sequentially passed through the anti-45kD column followed by passage through the anti-57-kD column. The columns were washed and adherent proteins were eluted as described in Example 6. The 45-kD and HypB proteins were eluted as homogeneous protein preparations as determined by immunoblotting and Coomassie brilliant blue and silver staining of SDS-PAGE gels (data not shown). Immunoblot probed with A, polyclonal anti-GPIC EB antiserum; B, anti-45kD mAb; and C, polyclonal monospecific anti-57-kD antiserum. Lane 1, GPIC EBs; lane 2, soluble Triton X-100 extract of GPIC EBs; lane 3, TX-100 extract after passage through the anti-45-kD affinity column; lane 4, antigens eluted from the anti-45-kD column; lane 5, TX-100 extract after passage through the anti-45-kD and anti-57-kD column; lane 6, antigens eluted from the anti-57-kD affinity column.

FIG. 13. Reactivity of monoclonal anti-HypB antibodies (mAbs). The genus specificity of the mAbs was shown using Western blot assay. All mAbs reacted with both the native chlamiydial HypB protein; lanes 1 and 5, and the recombinant HypB protein lanes 2 and 4. However, the mAbs did not react with the homologous E. coli protein (lane 3).

FIG. 14. Species specificity of the moncolonal antibodies is demonstrated using Western blot assay.

FIG. 15. Hematoxylin and eosin-stained sections of the palpebral conjunctiva from ocular immune guinea pigs 24 h after challenged with (A) TX-100 buffer; (B) soluble TX-100 extract of GPIC EBs; (C) immunoaffinity-purified HypB protein; and (D) TX-100 extract of GPIC EBs depleted of the HypB and 45-kD proteins. See footnotes to Table I (Example 7) for dosages of antigen administered. M, mucosal epithelium; SM, submucosa; P, polymorphonuclear neutrophil; L, lymphocyte, M$\phi$, macrophage.

DETAILED DESCRIPTION

Figure 8:
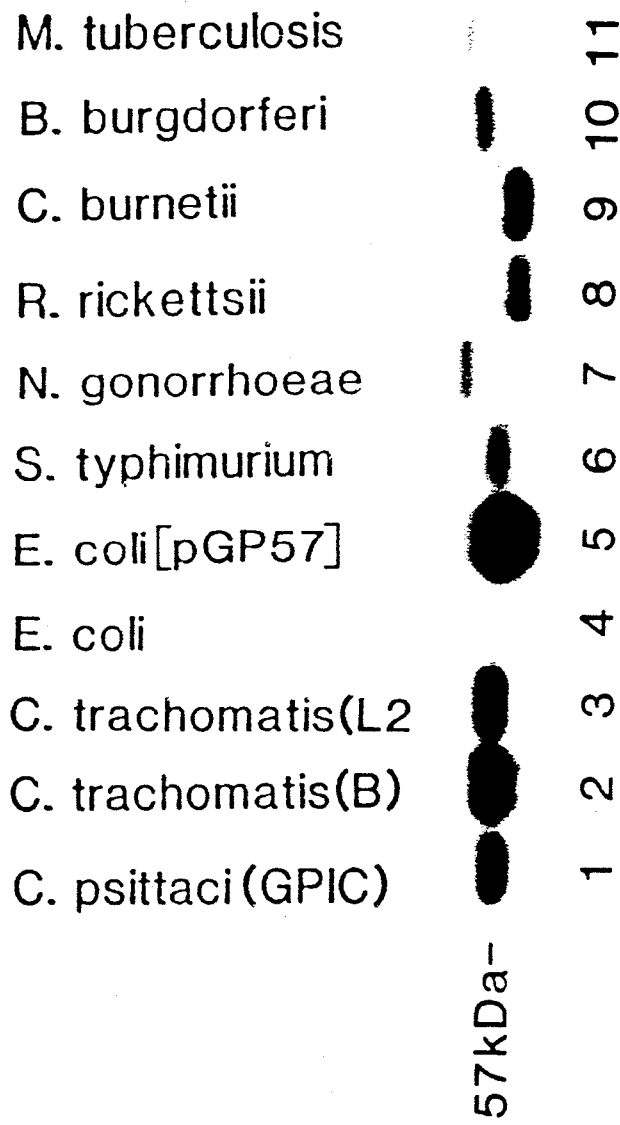

The present invention relates to segments of DNA which encode a HypB protein and a HypA protein derived from the bacteria Chlamydia, and to unique portions (i.e., at least 15 nucleotides) of such segments. The HypB proteins of C. psittaci and C. trachomatis have a molecular weight, as determined by sequence analysis, of about 58 kilo Daltons (kD). These HypB proteins have the same characteristics, function and are about 95% homologous. The HypA proteins of the two species have a molecular weight as determined by sequence analysis of about 12 kD.

The invention also relates the HypB chlamydial bacterial protein encoded in the hyp B gene, which is characterized as follows: (a) it is endogenous to and extractable from chlamydial elementary bodies (EBs) and reticulate bodies (RBs), (b) it produces delayed ocular and dermal inflammatory responses in mammals, (c) it is reactive with antiserum produced by antigens extracted from chlamydial EBs, (d) it can be purified essentially free of other material by standard biochemical and immunological techniques, (e) it has a molecular weight in SDS PAGE gels of about 57,000 D, (f) it is highly soluble, (h) it is very immunogenic. (i) it contains chlamydial specific epitopes, and (j) it contains epitopes common to other ca. 60kD stress-response proteins. In one embodiment, the protein of the invention has the amino acid sequence set forth in FIG. 5. In another embodiment, the HypB protein of the present invention has the amino acid sequence as set forth in FIG. 7. Indeed, the chlamydial HypA and HypB proteins are homologues of the *E. coli* GroES and GroEL heat shock proteins (HSP), respectively; and the HypB protein is a member of a widely conserved family of prokaryotic and eukaryotic stress response proteins referred to as HSP60.The invention also relates to unique portions of the HypB chlamydial bacterial protein described above, for example, a unique portion (at least 5 or 6 amino acids) of the sequence set forth in FIG. 5 or FIG. 7. The HypB protein substantially free of proteins with which it is normally associated can be bound to a solid support such as, for example, agarose, sepharose, plastic, nylon membrane or nitrocellulose paper.

The HypA protein encoded in the hyp A gene has a molecular weight in SDS PAGE gels of about 18,000 to 20,000 D. In one embodiment, it has the amino acid sequence as set out in FIG. 5, or a unique portion thereof. In another embodiment, it has the amino acid sequence as set forth in FIG. 7, or a unique portion thereof.

The present invention also relates to a recombinant DNA molecule comprising a vector and the above-described DNA segment which encodes at least the HypB protein or unique portion thereof. Possible vectors include plasmids, for example pUC8, and other vectors known in the art host cells stably transformed or transfected with the above-described recombinant DNA molecule in a manner which allows expression of the hyp proteins, fragment or analog. Examples of appropriate host cells include prokaryotic and eukaryotic cells depending on the vector used.

In another embodiment, the present invention relates to a process for the production of a polypeptide product having part or all of the primary structural conformation and/or biological activity of the naturally occurring hyp chlamydial proteins comprising growing host cells transformed or transfected with the above-described recombinant DNA molecule (for example pGP57) in a manner which allows the expression of the hyp B gene and thereby, production of the polypeptide product, and isolating the desired polypeptide product.

In another embodiment, the present invention relates to antibodies (monoclonal and polyclonal) specific for the HypB chlamydial antigen. Monospecific polyclonal antisera of the invention reacts with eukaryotic or prokaryotic antigens with molecular weights of approximately 57-kD and with proteins analogous to the chlamydial-specific determinant. The invention further relates to antibodies specifically for HypA chlamydial protein. The antibodies of the invention can be prepared using methods known in the art. The antibodies can be bound to a solid support such as, for example, agarose, sepharose, plastic nylon membranes or nitrocellulose paper. Antibodies can be prepared using, for example, native HypB, recombinant HypB, unique recombinant portions of HypB and synthetic peptides.

The present invention also relates to the detection of Chlamydia in a sample. The sample can be a clinical specimen, such as a swab of an infected site, or a cell culture. The presence of a chlamydial HypA or HypB protein is detected by contacting a reagent which specifically reacts with the protein with the sample under conditions such that a reaction can be effected and detected. Possible reagents include antibodies specific for the protein.

The presence of a DNA or RNA sequence encoding a chlamydia HypA or HypB protein is detected by contacting a labelled DNA probe which hybridizes to the sequence with the sample under conditions such that hybridization occurs and is detected.

The present invention also relates to a vaccine for use in mammals against chlamydial disease. In one embodiment of this aspect of this invention, as is customary for vaccines, the HypB protein of the present invention can be delivered to mammal in a pharmacologically acceptable vehicle. As one skilled in the art will understand, it is not necessary to use the entire protein. A unique portion of the protein (for example, a recombinantly produced polypeptide corresponding to a portion of the HypB protein) can be used. Vaccines of the present invention can include effective amounts of immunological adjuvants known to enhance an immune response. The protein or polypeptide is present in the vaccine in an amount sufficient to induce an immune response against the antigenic protein and thus to protect against chlamydia infection. Protective antibodies are usually best elicited by a series of 2-3 doses given about 2 to 3 weeks apart.

The series can be repeated when circulating antibodies concentration in the patient drops.

The invention is described in further detail in the following non-limiting Examples.

EXAMPLE 1

Construction of Genomic Library, Selection, Subcloning and Sequencing

*C. psittaci* (GPIC) genomic DNA isolated from $6\times10^{10}$ IFU, was partially digested with Sau3A, and sized by electrophoresis on a 0.7% agarose gel (Nano, et al., Infect. Immun., 48, 372 (1985)). 5 to 10-kilobase (kb) fragments were electroeluted and ligated into BamHI-digested, alkaline phosphate-treated pUC8 (Boehringer Mannheim Biochemicals, Indianapolis, Ind.) (Vieira, et al., Gene, 19, 259 (1982)). *E. coli* strain JM109 was transformed with the recombinant plasmids, grown in Luria broth supplemented with 250 ug/ml of carbenicillin, and screened by colony blot using hyperimmune anti-GPIC rabbit serum (Hanahan, J. Mol. Biol., 166, 557 (1983). Helfman, et al., Proc. Natl. Acad. Sci. (USA), 80, 31 (1983)). An immunoreactive clone, JM109 [pGP57], was isolated and analyzed by SDS-PAGE and immunoblotting. Two highly expressed recombinant products, 57-kD and 20-kD polypeptides, were visualized in Coomassie blue-stained gels of whole-cell lysates (FIG. 2). The 7.2-kb GPIC insert pGP57 was restriction mapped (FIG. 1) and shown to hybridize with GPIC DNA by Southern blot analysis. An internal 2.0-kb EcoRI fragment (E1) was subcloned into pTZ18R and shown to produce an immunoreactive polypeptide of 50 kD, presumably a truncated version of the 57-kD protein found in pGP57. A partial sequence of the 2.0-kb chlamydial DNA fragment from the E1 subclone was obtained by the dideoxy-chain termination method using pUC forward and reverse universal primer following the manufacturer's suggested procedures (Sequenase, United States Biochemical Corp., Cleveland, Ohio). After obtaining a partial DNA sequence from the E1 subclone, sequencing was continued using synthetic oligonucleotide primers (SAM1, Milligen-Biosearch, Inc., San Rafael, Calif.), and purified pGP57 plasmid DNA.

The cloning and sequencing methods described above were also performed using C. trachomatis serovar A genomic DNA. In the C. trachomatis experiments the plasmid pUC18 was used as the cloning vector. E. coli strain JM109 was tranfected with the recombinant pUC18 plasmids. An immunoreactive clone, JM109[pTA571], was isolated and analyzed in the same manner as clone JM109[pGP57].

Sequence Analysis

A 2.4-kb GPIC DNA insert of pGP57 carries two open reading frames (ORF) whose deduced amino acid sequences are presented in FIG. 5. Sequences consistent with Shine-Dalgarno ribosomal binding sites (AGGA) preceded the ATG initiation codons of both ORFs. One ORF spanned 306 nucleotides and encoded a polypeptide of 102 amino acids [relative molecular mass ($M_r$) 11,202], and the other spanned 1,632 nucleotides to encode a polypeptide of 544 amino acids ($M_r$ 58,088).

The serovar A DNA insert of pTA571 also carries two ORF whose deduced amino acid sequences are shown in FIG. 7. One ORF has a relative molecular mass of 17,000 daltons and the other ORF has a relative molecular mass of 57,000 daltons on denaturing SDS-polyacrylamide gels.

Because the 57-kD protein has a single known function, its ability to elicit an immunopathological response in primed animals (a DH response), the whole operon has been termed hyp (for hypersensitivity); C. psittaci hypA encodes the 11.2-kD protein and hypB encodes the 58.1-kD protein. The apparent molecular mass of HypA and HypB proteins on denaturing polyacrylamide gels is 20 kD and 57 kD, respectively. The presumptive TAA translational terminator sequence of hypA was followed by an intergenic region of 50 bases. The larger ORF, hypB, terminated at a TAA stop codon followed by sequences resembling a rho-independent terminator (Platt, Cell, 24, 10 (1981)).

The nucleotide sequence of the hyp operon from C. trachomatis serovar A is shown in FIG. 7. The operon contains two open reading frames (hyp A and hyp B), which encode polypeptides of calculated molecular weights of approximately 11.1 kD (HypA) and 58 kD (HypB). The deduced amino acid sequences of the C. trachomatis serovar A HypA and HypB polypeptides are shown in FIGS. 7, 9 and 10.

At nucleotide position −231 of the C. psittaci hyp operon sequence like a heat shock promoter (−35 region, T-C-C-CTTGAA, −10 region, CCCCAT-T-) was found (Christman, et al., Cell, 41, 753 (1985)). There was considerable sequence agreement for the −10 region, with only a single G for C substitution. The 3' end of the −35 region was in complete agreement, but the 5' half was not conserved. No other upstream consensus promoter regions were found. Although this inferred promoter region has similarities with promoters of genes for other heat-shock proteins, a temperature dependent expression of the polypeptides encoded by this recombinant operon in E. coli has not been demonstrated. Expression of the two proteins in bacteria grown at 22° C. is high, and may result from the high copy number of pGP57.

Because of the tandem hypA and hypB ORFs and their striking resemblance to the E. coli. groE and the C. burnetti htp operons, Northern hybridizations were done to determine whether both hypA and hypB sequences were contained in a single transcript. Oligonucleotide probes complementary to the 5' end of hypA, and the 3' end of hypB (FIG. 5) revealed that hypA and hypB are expressed as a single mRNA transcript of ≈2300 nucleotides.

Predicted Amino Acid Sequence Homology

The amino acid sequence encoded by the C. psittaci HypA protein showed identify with HtpA (42%) and GroES (38%) proteins (FIG. 6A) (Hemmingsen, et al., Nature, 333, 330 (1988); Vodkin et al., J. Bacteriol., 170, 1227 (1988)). The C. psittaci HypB protein showed more identity to the HtpB protein of C. burnetii (61%), the GroEL protein of E. coli (60%), the 65-kD protein of M. tuberculosis (58%), and the mature Hsp60 protein of S. cerevisiae (53%) (Vodkin, supra. Hemmingsen, supra. Shinnick, J. Bacteriol., 169, 1080 (1987). Reading, et al., Nature, 337, 655 (1989)). Regions of identity were scattered throughout the sequence. However, the N− and C− terminal sequences, sequence 318 to 361, and sequence 421 to 481 exhibited more divergence and may be determinants of the polypeptide that specify chlamydial-specific epitopes. The predicted amino acid sequence of the C. trachomatis HypA and HypB proteins were 85 and 94% identical with the C. psittaci HypA and HypB proteins, respectively (FIG. 9 and 10).

Because the 57-kD chlamydial protein showed considerable amino acid identity with the common GroEL antigen of E. coli., other prokaryotic organisms were examined by immunoblotting with anti-57-kD serum (FIG. 8). This antiserum reacted with polypeptides of similar $M_r$ ($M_r$=molecular weight determined in SDS PAGE gels) in all bacteria examined. These results along with the amino acid homologies demonstrate that the 57-kD chlamydial protein is a member of the family of widely conserved stress-response proteins referred to as common antigen (Hoiby, Scand. J. Immunol., 4(2), 187 (1975)).

EXAMPLE 2

Antigen Preparation, Purification and Ocular DH.

$10^9$ chlamydial elementary bodies were washed three times with saline, resuspended in 10 ml of PBS containing 0.5% Triton X-100 (TX-100), incubated at 37° C. for 30 min and sonicated for 3 to 5 min. (Watkins supra). Insoluble material was removed by centrifugation at $100,000 \times g$ and the HypB protein was purified from the soluble extract by immunoaffinity chromatography (Morrison, supra). Briefly, the soluble extract of chlamydial elementary bodies was passed over an affinity column prepared with monospecific anti-57-kD rabbit serum. Morrison, supra. The column was washed with 10 volumes of PBS containing 0.5% Triton X-100 and 0.5 M NaCl. Absorbed antigen was eluted with 3.0M potassium thiocyanate, dialyzed against PBS, and analyzed by SDS-PAGE and immunoblotting. A single 57-kD polypeptide was seen by Coomassie blue staining, and it reacted with monospecific anti-57-kD serum by immunoblot analysis.

The ability of these antigen preparations to elicit an ocular DH response was assessed by placing 25 μl of antigen preparation (2 to 6 μg of protein) onto the lower conjunctival sac of ocular immune guinea pigs (Morrison, supra). The hypersensitivity response was assessed clinically at 24 h, and scored using a scale of 0 to 4: 0, negative; 1, slight hyperemia and edema of the lower palpebral conjunctivae; 2, hyperemia and edema of the lower palpebral conjunctiva with slight hyperemia of the bulbar conjunctivae; 3, overt hyperemia and edema of the lower palpebral and bulbar conjunctivae; 4, same as 3 with the addition of mucopurulent exudate (Morrison, supra).

Ocular Delayed Hypersensitivity Elicited by the Recombinant HypB Protein.

Immune guinea pigs, previously infected with GPIC and recovered, were challenged with a soluble extract of JM109, JM109[pGP57] or the immunoaffinity purified recombinant HypB antigen (purified as described for elementary bodies i.e. above in example 2). Both the soluble extract of JM109[pGP57] and the purified recombinant HypB protein elicited an ocular DH response when administered topically to the conjunctivae of immune but not naive guinea pigs (FIG. 4). Severity of inflammation resembled that elicited by a crude extract of *C. psittaci* EBs and immunoaffinity purified native 57-kD protein.

EXAMPLE 3

Production of the Recombinant Polypeptide Products

Organisms

The *C. trachomatis* serovars B/TW-5 and L2/LGV-434, and *C. psittaci* strain guinea pig inclusion conjunctivitis (GPIC) were grown in HeLa 229 cells, and EBs were purified by discontinuous density centrifugation in Renografin (E. R. Squibb and Sons, Princeton, N.J.) (Caldwell, et al., Infect. Immun. 31,1161 (1981). Inclusion-forming units (IFU) were determined by methods described in Sabet, et al. (J. Clin. Microbiol., 20, 217 (1984)). *E. Coli* strain JM109, and pUC8 and pTZ18R plasmids have been described previously by Yanisch-Perron, et al. (Gene, 33,103 (1985), Vieira at 259, supra, and Pharmacia LKB Biotechnology, Inc. Piscataway, N.J.).

Identification and Characterization of Recombinant Clones

Recombinant colonies were screened by blotting with a polyclonal antiserum to GPIC. One recombinant, JM109[pGP57], expressed two products with apparent molecular weights of 57 kD and 20 kD (FIG. 2A); the 57-kD species reacted with a polyclonal monospecific anti-57-kD serum by immunoblotting (FIG. 2B). An *E. coli* polypeptide of the same size was also recognized by this antiserum. To verify that the 20- and 57-kD polypeptides were encoded by the plasmid and were not due to an increased expression of the *E. coli* proteins, in vitro transcription-translation was done. The recombinant plasmid, pGP57, encoded two polypeptides of 57 kD and 20 kD (FIG. 3), and the in vitro synthesized 57-kD polypeptide immunoprecipitated with anti-57-kD serum. A recombinant clone expressing polypeptides similar to those of pGP57 has been briefly described elsewhere (Menozzi, et al., FEMS Microbiol. Lett., 58, 59 (1989)).

EXAMPLE 4

SDS-PAGE, Electrophoretic Transfer, and Immunoblotting

SDS-PAGE was performed using 12.5% polyacrylamide gels as described by Dreyfuss et al., except chlamydial whole-cell lysates and samples were prepared with 2 X Leammli sample buffer (Dreyfuss, et al., Mol. Cell. Biol., 4,415 (1984), Laemmli, Nature, 227,680 (1970)). The apparent molecular masses of chlamydial proteins recognized by the anti-57-kD and anti-45-kD antibodies were determined by comparing the migration distances of these immuno-reactive proteins with a plot of migration distance vs. the log molecular mass of several protein standards (Bio-Rad Laboratories, Richmond, Calif.). Electrophoretic transfer and processing were done as described by Zhang et al. J. Immunol., 138, 575 (1987)).

In Vitro Detection of Recombinant Polypeptides

In vitro transcription-translation of pGP57 was performed according to the manufacturers instructions (Amersham Corp., Arlington Heights, Ill.) $^{35}S$-methionine labelled products were analyzed by SDS-PAGE and fluorography as described in Bonner, et al. (Eur. J. Biochem., 46, 83 (1974) and Zhang, supra). The in vitro transcription-translation mixtures were also subjected to immunoprecipitation with a monospecific anti-57-kD rabbit serum or normal rabbit serum, and analyzed by SDS-PAGE and fluorography (Morrison, supra. Boner, et al., Eur. J. Biochem, 46, 83 (1974) and Zhang, supra).

Characteristics of Chlamydial Proteins

The SDS-PAGE polypeptide profile of the 15 serovars of *C. trachomatis* and two strains of *C. psittaci* are shown in FIG. 11 A. The HypB and 45-kD proteins are indicated by arrows and the MOMPs are the major staining protein bands that appear in the bracketed area of the gel. The genus specificity of the anti-57-kD and anti-45-kD antibodies are demonstrated in FIG. 11 B and C, respectively. The anti-57-kD antiserum reacted with a similar molecular mass protein in all chlamydial strains tested. Similarly, the anti-45-kD antibody reacted with all strains, although more strongly with the 45-kD protein of the *C. psittaci* strains GPIC and Mn. The weaker reactivity of the *C. trachomatis* strains might be explained by quantitative differences in this protein among strains or may simply reflect stronger reactivity to the immunizing species. Slight variability in M, of this protein among strains was also observed. These data demonstrate the genus specificity of the anti-57-kD and anti-45-kD antibodies, and the prominence of these proteins in chlamydial EBs.

EXAMPLE 5

Affinity Chromatography and Antigen Purification

The protein A binding fraction of a polyclonal monospecific rabbit antiserum against the genus-specific 57-kD chlamydial protein and a mAb (purified IgG), reactive against the 45-kD genus-specific chlamydial protein (GPIC-IV B1, IgG, a gift from Dr. You-Xun Zhang, Rocky Mountain Laboratories), were used to prepare the affinity columns. The polyclonal anti-57-kD antiserum was prepared by immunizing rabbits with isolated immunoprecipitin bands excised from two-dimensional immunoelectropherograms as described in Caldwell, et al. (J. Immunol. 115, 969 (1975)).

The immunopreciptates used as immunogen in the preparation of the anti-57-kD antiserum correspond to the single common crossreacting antigen observed by crossed immunoelectrophoresis (Caldwell at 963, supra). mAb GPIC IV-BI was prepared by immunizing BALB/c mice with GPIC EBs and following the procedures described in Caldwell, et al. (Infect. Immun., 44, 306 (1984)).

The purified antibodies were covalently crosslinked to the support matrix (Schrieder, et al., J. Biol. Chem., 257, 10766 (1982)). 1-ml packed volume of swollen protein A-Sepharose CL-4B (Sigma Chemical Co., St. Louis, Mo.) beads was gently mixed with 10 mg (at 1 mg/ml in 50 mM PBS, pH 7.2) of either anti-45-kD or anti-57-kD antibody at 22° C. for 45 min. The immunomatrix (protein A-Sepharose antibody) was washed three times with 100 mM borate buffer, pH 8.2, followed by a single 20-ml wash with 200 mM triethanolamine, pH 8.2. The antibody was covalently cross-linked to the protein A-Sepharose by resuspending the immunomatrix in 20 ml of freshly prepared 20 mM dimethylpimelimidate-dihydrochloride in 200 mM triethanolamine, pH 8.2, and gently mixed for 45 min at 22° C. The immunomatrix was pelleted by light centrifugation and resuspended in 1.0 ml of 20 mM ethanolamine, pH 8.2. After 5 min at 22° C., the immunomatrix was washed once with 10 ml of 100 mM borate buffer, pH 8.2, poured into a column, washed with 20 ml of PBS, and stored at 4° C. until used. The 45 and 57-kD chlamydial proteins were purified from a Triton X-100 soluble extract of GPIC EBs. Morrison, supra.

10 ml of the soluble GPIC extract was preabsorbed with 0.1 g of protein A-Sepharose for 45 min at 22° C. to remove nonspecifically binding components of the extract. The preabsorbed antigen extract was sequentially passed through the anti-45-kD and anti-57-kD and anti-57-kD columns, respectively. Each column was washed with 20 ml of 50 mM phosphate buffer, pH 7.2, containing 500 mM NaCl and 0.5% Triton X-100. Bound antigen was eluted with 3.0 M potassium thiocyanate (KSCN) in PBS. 1-ml fractions were collected, dialyzed overnight against PBS at 4° C., and analyzed for purity by SDS-PAGE and immunoblotting. Approximately 500 and 300 $\mu$g of protein were eluted from the anti-45-kD and anti-57-kD columns, respectively. Fractions containing purified protein were assayed for their ability to elicit ocular hypersensitivity as described above.

Immunoblot Analysis of Purified Chlamydial Antigens

Figure 12:
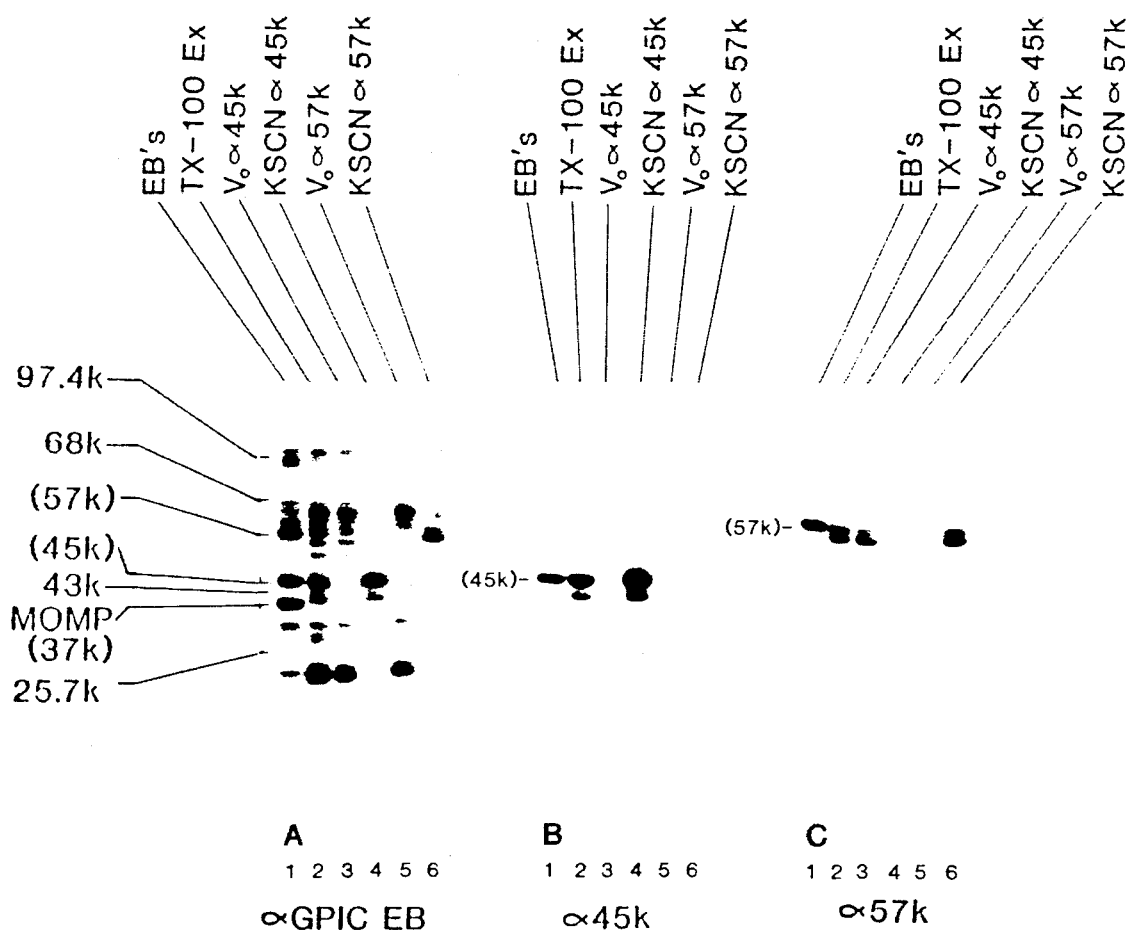

The 45-kD and HypB chlamydial proteins and LPS are genus-specific constituents and major components found in the soluble fraction of the TX-100 extract of GPIC EBs. This extract causes an ocular hypersensitivity response in ocular immune guinea pigs (Watkins, supra). Since a major genus-specific constituent of this extract (LPS) failed to induce ocular hypersensitivity, the extract was purified using immunoaffinity chromatography to obtain the 45-kD and HypB proteins (FIG. 12). The soluble TX-100 extract of GPIC EBs contains a number of immunoreactive proteins recognized by antiserum raised to GPIC EBs (FIG. 12, lane 2). Passage of this extract through the anti-45-kD column followed by passage through the anti-57-kD column efficiently removed the 45-kD and HypB proteins (FIG. 12, lanes 3 and 5, respectively). They were then eluted from the columns as antigenically homogeneous proteins (FIG. 12, lanes 4 and 6). Homogeneity of the protein preparations was also demonstrated by Coomassie brilliant blue and silver staining of SDS-PAGE gels. Noteworthy is the finding that both the 45-kD and HypB proteins migrate as single bands in EB preparations, but were observed as doublets in the extract and purified fractions.

EXAMPLE 6

Chlamydial Infection, and Ocular Hypersensitivity

Male and female Hartley guinea pigs, 8-12 wk old from a chlamydial-free colony, were used throughout these studies. Animals were bred and maintained at the Rocky Mountain Laboratories, Hamilton, Mont. Animals were infected by placing 10 $\mu$l containing 10 ID$_{50}$ ($10 \times 10^2$ IFU) of GPIC onto the lower conjunctiva as described in Watkins, supra.

Conjunctivae of infected guinea pigs were culture negative by 4 wk after infection. These guinea pigs are referred to as ocular immune and were used to test for ocular hypersensitivity 6-8 wk after primary infection. Ocular hypersensitivity was assessed by placing 25 $\mu$l of the appropriate antigen solution onto the lower conjunctival sac. The hypersensitivity response was assessed clinically at 2, 12, 18, 24, 48, and 72 h and was scored using a scale of 0 to 4 (Watkins, supra, Morrison, supra; pg. 14, supra). Peak inflammation was observed at 24 h after instillation of antigen. The time course of the inflammatory response and the nature of the cellular infiltrate (see FIG. 13) has led us to refer to this response as an ocular DH.

Ocular Hypersensitivity Elicited by Chlamydial Antigen Preparations

Chlamydial antigen preparations and affinity-purified proteins were tested for their ability to elicit an ocular inflammatory response in immune and naive guinea pigs (Table I). The purified HypB, but not the 45-kD chlamydial protein, elicited an inflammatory response when administered topically to the conjunctival surface of ocular immune guinea pigs. The intensity of the inflammatory response elicited by the purified HypB protein (3.1) was similar to that elicited by the soluble TX-100 extract (3.4). Depleting the extract of the 45-kD and HypB proteins did not render the extract noninflammatory. However, the intensity of the ocular inflammation was marginal (2.3) and waned more quickly than the response elicited by the extract containing these proteins.

TABLE I

Ocular-delayed Hypersensitivity Elicited by Chlamydial Antigen Preparations

| Challenge antigen preparation* | Clinical response+ (no. positive/no. tested) | |
|---|---|---|
| | Immune | Naive |
| C. psittaci (GPIC) TX-100 extract (lane 2) | 15:15 (3.4)§ | 0:6 (<1) |
| GPIC TX-100 extract $V_o$ anti-45 kD (lane 3) | 10:10 (3.3) | 0:6 (<1) |
| Purified 45-kD protein (lane 4)# | 1:10 (<1) | 0:6 (<1) |
| GPIC TX-100 extract $V_o$ anti-57 kD (lane 5) | 10:10 (2.2) | 0:6 (<1) |
| Purified 57-kD protein (lane 6)# | 9:10 (3.1) | 0:6 (<1) |
| TX-100 buffer | 0:6 (<1) | 0:6 (<1) |

*Purified GPIC EBs ($10^{10}$ IFU) were extracted with 10 ml of 25 mM PBS containing 0.5% Triton X-100 for 30 min at 37° C. and centrifuged at 100,000 g for 1 h. The resulting soluble extract was used as hypersensitivity antigen. Fractions of this antigen preparation, corresponding to those described in FIG. 2, were tested for hypersensitivity. Guinea pigs were challenged by placing 25 μl of antigen preparation onto the lower conjunctival sac. Animals challenged with the GPIC TX-100 extract or column passed extracts received ~6-8 μg of protein. Those challenged with the purified 45- or 57-kD proteins received ~1-2 μg of protein.
+Ocular hypersensitivity was assessed 24 h after challenge. Inflammation was scored on a scale of 0 (negative) to 4 (overt hyperemia and edema of the conjunctiva with mucopurulent exudate). A clinical score of 2 was considered positive. Data are presented as the number of guinea pigs eliciting a positive ocular hypersensitivity response (clinical score >2.0) over the total number tested.
§Mean clinical score
Purified 45- and 57-kD proteins were mixed 1:1 with 2X Triton X-100 buffer before use.
‡PBS + 0.5% Triton X-100.

EXAMPLE 7

Monoclonal Antibodies to the HypB Protein.

Figure 13:
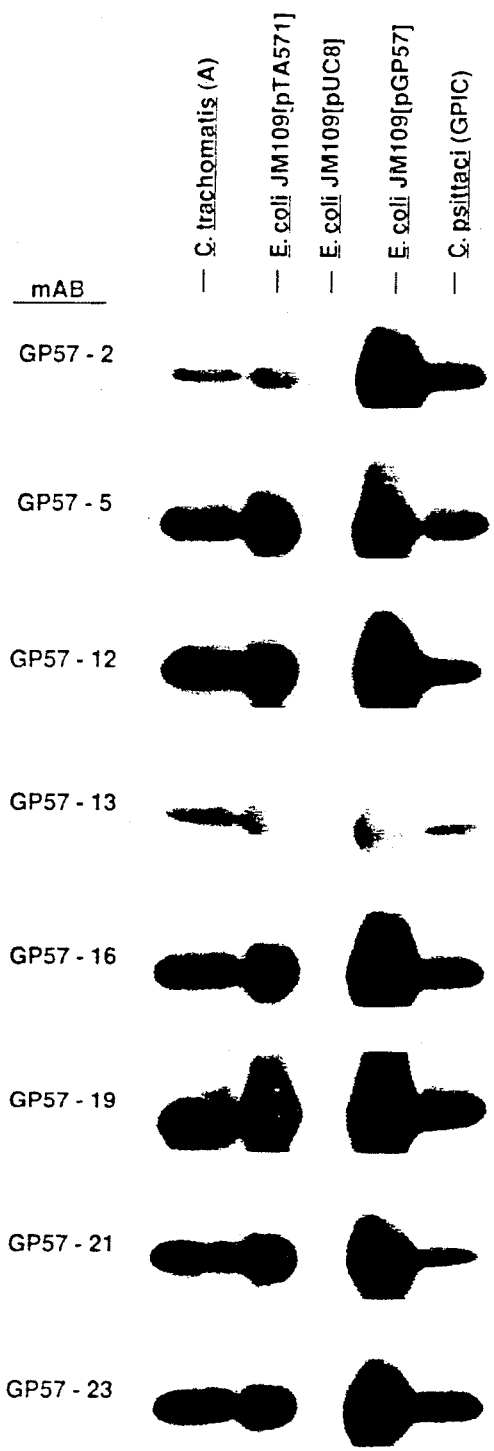
Figure 14:
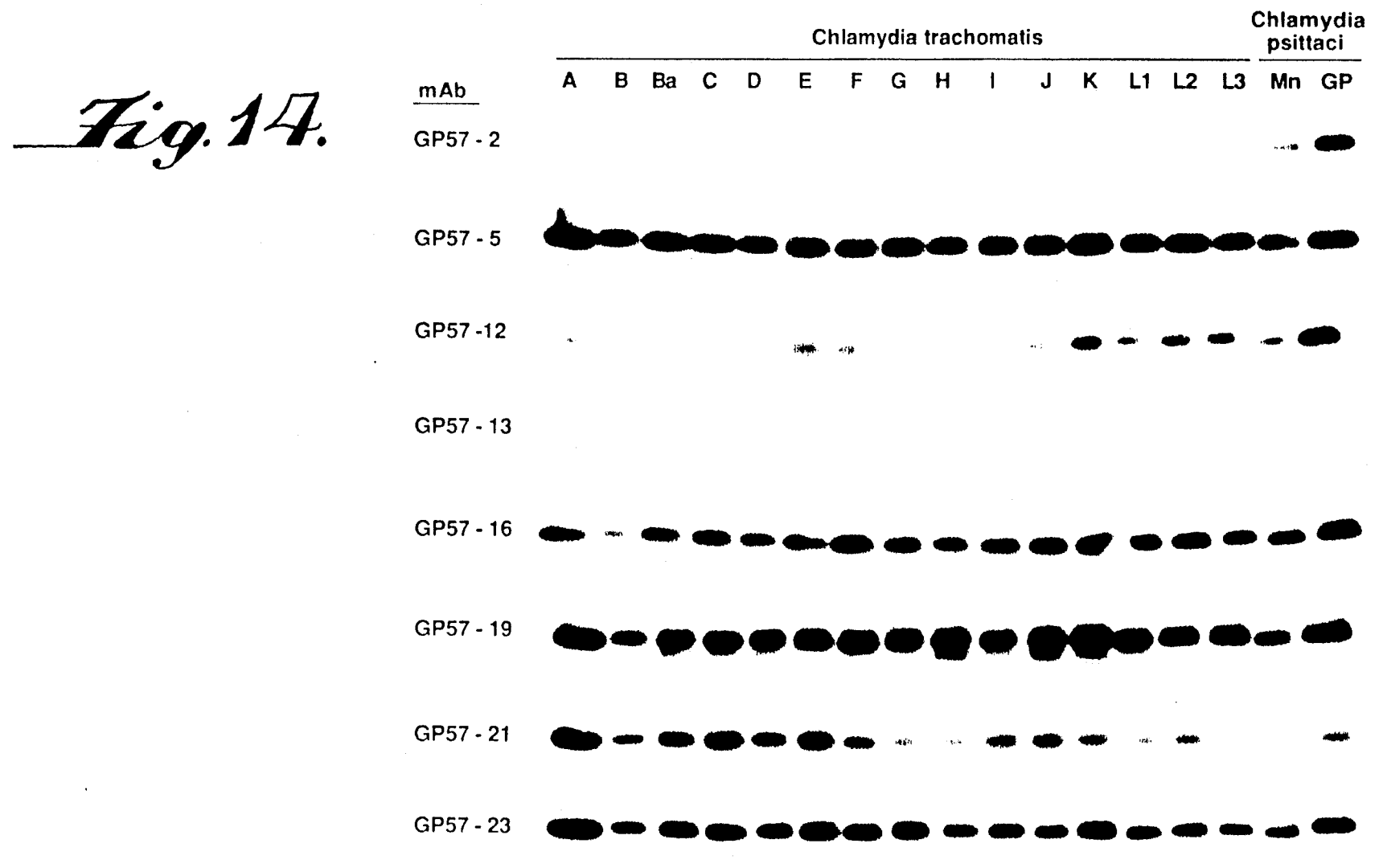
Figure 15B:
Figure 15D:
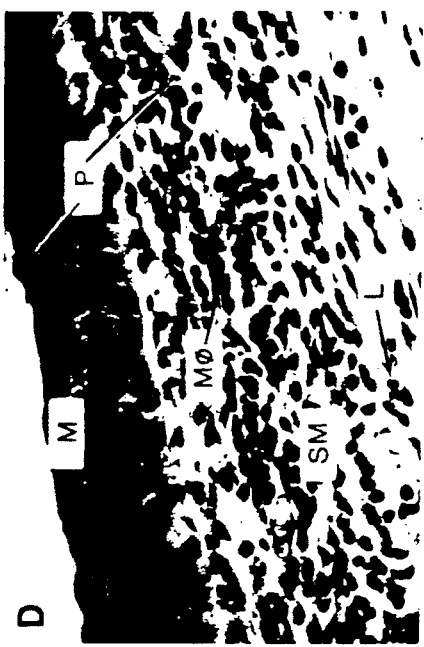
Figure 15A:
Figure 15C:
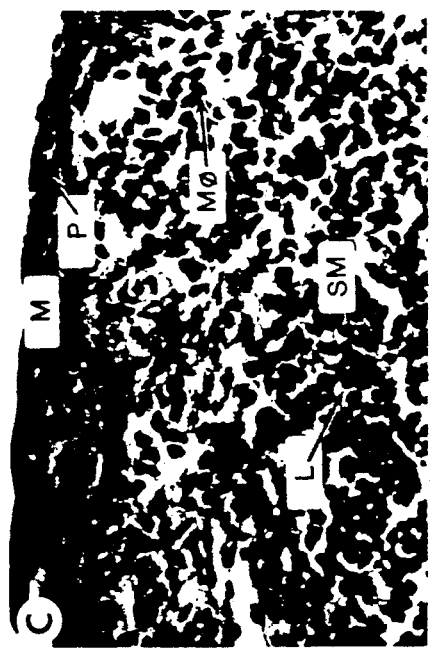

The HypB protein was isolated from the recombinant clone (JM109[pGP57]) by SDS-polyacrylamide gel electrophoresis and electroelution, and used to immunize BALB/C mice. Hybridomas secreting anti-57kD antibodies were produced by fusing splenic lymphocytes from immunized mice with murine myeloma cells (P3-NS-1-AG-4/1) using standard procedures (Caldwell, et al. Infec. Immun. 44: 306 (1984)). Eight monoclonal antibodies were isolated, all of which are of the IgG$_1$ isotype. The reactivity of the mAbs using Western blot assay is shown in FIGS. 13 and 14. FIG. 13 demonstrates the genus specificity of the mABs. All mABs reacted with the chlamydial protein, that is, both the native HypB protein found associated with chlamydial organisms, lanes 1 and 5, and the recombinant HypB proteins, lanes 2 and 4, but failed to react with the homologous protein found in E. coli. (lane 3).

FIG. 14 illustrates the species specificity of the mABs. mABs GP57-5, GP57-16, GP57-19 and GP57-23 react equally well with all C. trachomatis serovars and the two C. psittaci strains and mABs GP57-12 and GP57-21 vary in reactivity among C. trachomatis and C. psittaci strains.

EXAMPLE 8

The C. trachomatis serovars A/Har-13, B/TW-5, Ba/Apa-2, C/TW-3, D/UW-31, E/Bour, F/IC-Cal-13, G/UW-57, H/UW-4, I/UW-12, J/UW-36, L1/LGV-440, L2/LGV-434, and L3/LGV-404, C. psittaci strains guinea pig inclusion conjunctivitis (GPIC), and meningopneumonitis (Mn) were grown in HeLa 229 cells, and EBs were purified by discontinuous density centrifugation in Renografin (E. R. Squibb and Sons, Princeton, N.J.) (Caldwell, et al., Infect. Immun., 31, 1161 (1981)). Inclusion-forming units (IFU) were determined by methods described previously). (Sabet, supra).

Histology

Guinea pigs were killed with T-61 euthanasia solution (Hoechst Corp., Somerville, N.J.). The upper and lower eyelids were removed, fixed in neutral-buffered 10% formalin, and stained with hematoxylin and eosin as described in Watkins, supra.

Histological Profile of Ocular Hypersensitivity Responses

To determine the cellular characteristics of the inflammation elicited by the various antigen preparations, hematoxylin- and eosin-stained sections of the palpebral conjunctiva were examined at the time of peak inflammation (24 h post-challenge) (FIG. 15). The inflammatory response elicited by the soluble TX-100 extract and the purified genus-specific HypB protein were indistinguishable (FIG. 15, B and C). Both these preparations elicited a subacute inflammatory response characterized by lymphoid hyperplasia and a submucosal infiltrate consisting primarily of mononuclear macrophages and lymphocytes. Occasional polymorphonuclear neutrophils (PMN) were observed at the mucosal surface.

In contrast, the inflammatory response elicited by the extract depleted of the 45-kD and HypB proteins was more acute and characterized by a marked PMN infiltrate (FIG. 15 D).

In some instances, DH responses in the guinea pig have been shown to the examples of cutaneous basophil hypersensitivity. In fact, certain antigens elicit conjunctival cutaneous basophil hypersensitivity (Allansmith, et al., J. Allergy Clin. Immunol., 78, 919 (1986)). Therefore, Giemsa-stained sections of the palpebral conjunctiva from chlamydial-antigen-challenged guinea pigs were examined for the presence of basophils. Only very few basophils (1%) were observed in the infiltrates. Thus, because the inflammatory response elicited by the TX-100 extract and the purified HypB protein was primarily mononuclear (macrophage and lymphocyte) and delayed in appearance (24 h), we have characterized it as an ocular DH.

Hybridomas producing monoclonal antibodies to the HypB protein were deposited on April 4, 1990 under the Budapest Treaty at the American Type Culture Collection, 12301 Parklawn Drive, Rockville, Md. 20852. mAb19-2E1 referred to as mAB GP57-19, hereinabove and mAb5-2G9 referred to as mAB GP57-5, hereinabove were assigned the accession number ATCC HB10407 and ATCC HB10408 respectfully.

While the foregoing invention has been described in some detail for purposes of clarity and understanding, it will be clear to one skilled in the art from a reading of this disclosure that various changes in form and detail can be made without departing from the true scope of the invention.

What is claimed is:

1. A monoclonal antibody which binds to the Chlamydial HypB protein genus-associated epitopes bound by monoclonal antibody GP57-5.

2. A monoclonal antibody which binds to the Chlamydial HypB protein genus-associated epitopes bound by monoclonal antibody GP57-19.

3. A monoclonal antibody having all the identifying characteristics of monoclonal antibody GP57-19 produced by the hybridoma cell line with the accession number ATCC HB10407.

4. A monoclonal antibody having all the identifying characteristics of monoclonal antibody GP57-5 produced by the hybridoma cell line with the accession number ATCC HB10408.

* * * * *